(12) United States Patent
Suddaby

(10) Patent No.: US 11,109,897 B2
(45) Date of Patent: Sep. 7, 2021

(54) EXPANDABLE FACET JOINT FIXATION DEVICE

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 203 days.

(21) Appl. No.: 16/053,205

(22) Filed: Aug. 2, 2018

(65) Prior Publication Data

US 2020/0038070 A1 Feb. 6, 2020

(51) Int. Cl.
*A61F 2/44* (2006.01)
*A61B 17/70* (2006.01)
*A61B 17/16* (2006.01)

(52) U.S. Cl.
CPC ...... *A61B 17/7065* (2013.01); *A61B 17/1671* (2013.01); *A61B 17/7064* (2013.01); *A61F 2/4405* (2013.01)

(58) Field of Classification Search
CPC ............ A61B 17/7064; A61B 17/7065; A61B 17/7098; A61B 17/7258; A61B 17/7266; A61B 17/7275; A61B 17/7291; A61B 17/844; A61B 17/885; A61B 17/8852; A61B 17/8858; A61B 2017/8655; A61F 2002/30579
See application file for complete search history.

(56) References Cited

U.S. PATENT DOCUMENTS

| 5,390,683 | A | 2/1995 | Pisharodi |
| 6,039,761 | A | 3/2000 | Li et al. |
| 6,224,604 | B1 | 5/2001 | Suddaby |
| 6,520,991 | B2* | 2/2003 | Huene ............... A61F 2/446 623/17.11 |
| 7,070,598 | B2 | 7/2006 | Lim et al. |
| 7,513,900 | B2* | 4/2009 | Carrison ............ A61B 17/885 606/279 |
| 8,062,375 | B2 | 11/2011 | Glerum et al. |
| 8,080,046 | B2 | 12/2011 | Suddaby |
| 8,551,171 | B2* | 10/2013 | Johnson ............ A61B 17/844 606/279 |
| 8,771,277 | B2 | 7/2014 | Zappacosta et al. |
| 8,864,833 | B2 | 10/2014 | Glerum et al. |
| 8,998,992 | B2 | 4/2015 | Siefert et al. |

(Continued)

FOREIGN PATENT DOCUMENTS

| WO | WO2001/01895 | 1/2001 |
| WO | WO2010/103344 | 9/2010 |

*Primary Examiner* — Lynnsy M Summitt

(74) *Attorney, Agent, or Firm* — Simpson & Simpson, PLLC; Michael Nicholas Vranjes

(57) ABSTRACT

An expandable facet joint fixation device, including a first collar, a central shaft including a first end and a second end, the first end rotatably connected to the first collar, a second collar including a radially inward facing surface, the second collar concentrically arranged around the central shaft, and one or more expandable members, each of the one or more expandable members including a first arm hingedly connected to the first collar, a second arm hingedly connected to the second collar, the second arm hingedly connected to the first arm, wherein when the second collar is displaced in a first axial direction relative to the first collar, the one or more expandable members displace radially outward in a first radial direction.

19 Claims, 17 Drawing Sheets

(56) References Cited

U.S. PATENT DOCUMENTS

| | | | |
|---|---|---|---|
| 9,028,496 B2* | 5/2015 | Tontz | A61B 17/7233 |
| | | | 606/64 |
| 9,034,041 B2* | 5/2015 | Wolters | A61B 17/8858 |
| | | | 623/17.15 |
| 9,220,535 B2* | 12/2015 | Robling | A61B 17/7001 |
| 9,358,131 B2* | 6/2016 | Lorio | A61F 2/447 |
| 9,364,339 B2* | 6/2016 | Mayer | A61F 2/442 |
| 9,622,872 B2 | 4/2017 | McKay | |
| 9,724,141 B2* | 8/2017 | Thornes | A61B 17/746 |
| 9,795,428 B2* | 10/2017 | Levy | A61B 17/7035 |
| 2004/0087994 A1* | 5/2004 | Suddaby | A61B 17/8858 |
| | | | 606/190 |
| 2006/0100706 A1* | 5/2006 | Shadduck | A61B 17/1617 |
| | | | 623/17.11 |
| 2006/0116689 A1* | 6/2006 | Albans | A61B 17/1671 |
| | | | 606/92 |
| 2009/0281628 A1 | 11/2009 | Oglaza et al. | |
| 2010/0100135 A1* | 4/2010 | Phan | A61B 17/7064 |
| | | | 606/301 |
| 2010/0145396 A1 | 6/2010 | Thornes | |
| 2010/0168748 A1* | 7/2010 | Knopp | A61B 18/1482 |
| | | | 606/79 |
| 2012/0071977 A1* | 3/2012 | Oglaza | A61B 17/7065 |
| | | | 623/17.11 |
| 2014/0135780 A1* | 5/2014 | Lee | A61F 2/4601 |
| | | | 606/94 |
| 2016/0081724 A1* | 3/2016 | Robling | A61B 17/7001 |
| | | | 606/279 |

* cited by examiner

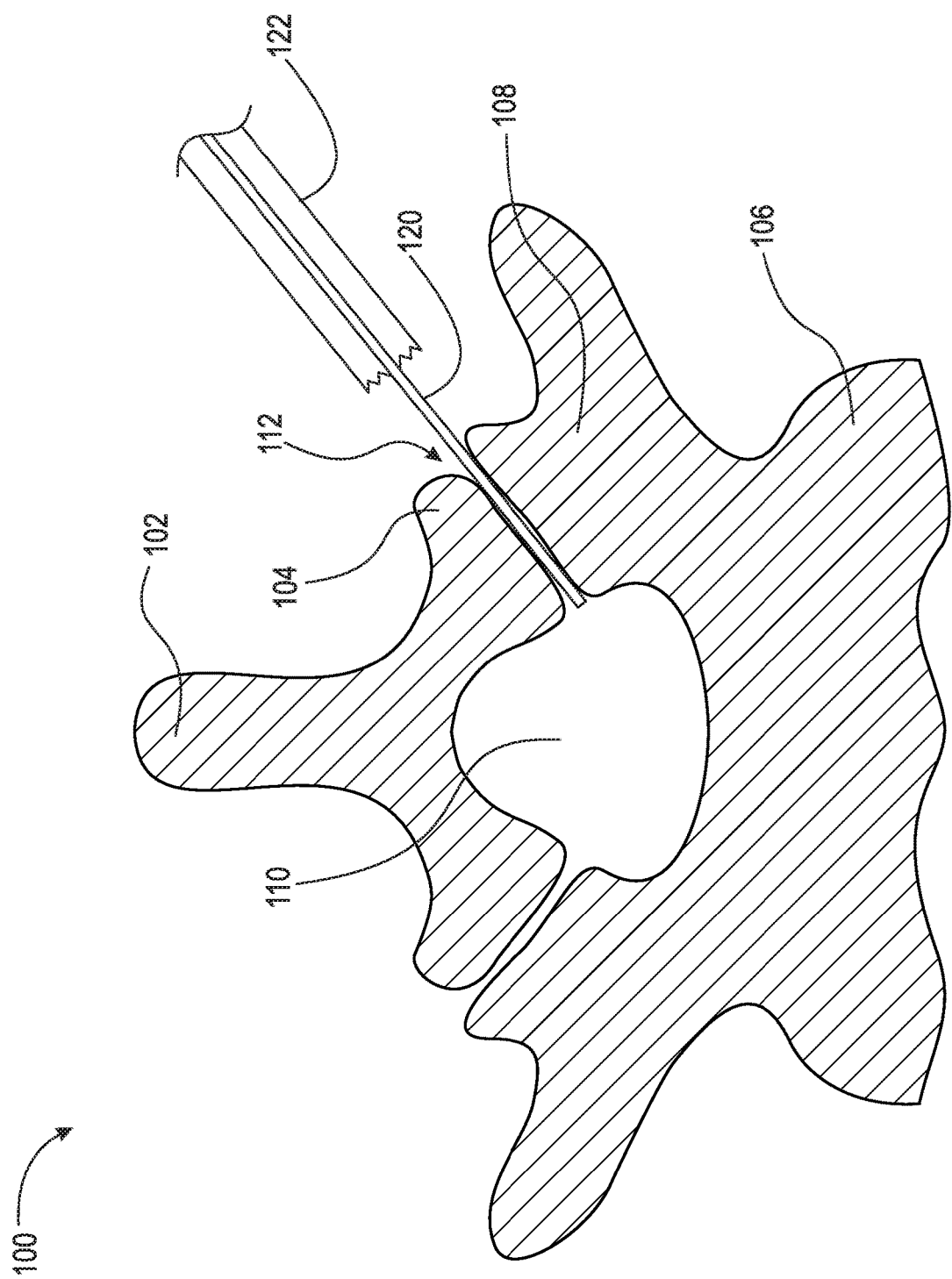

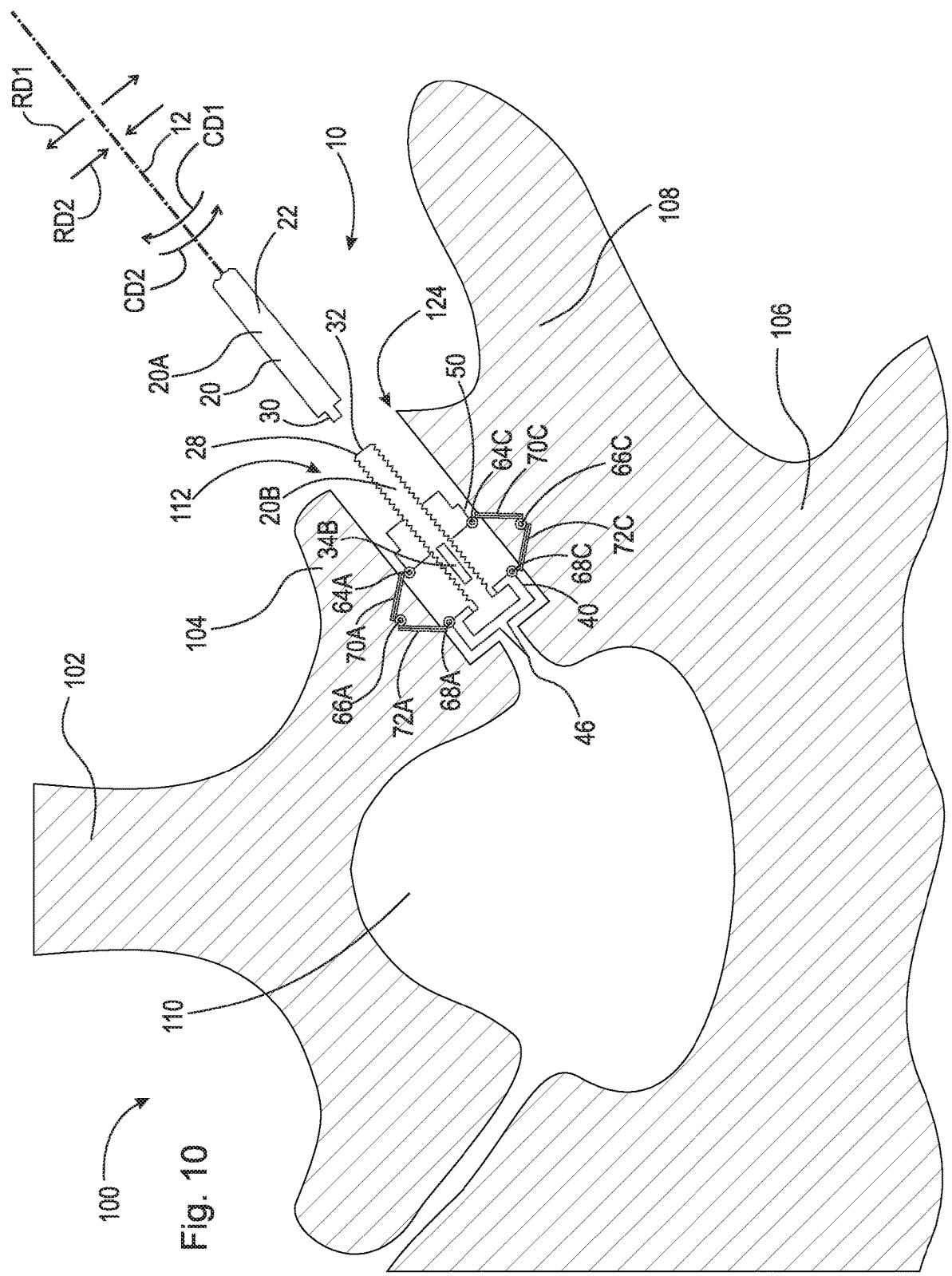

EXPANDABLE FACET JOINT FIXATION DEVICE

FIELD

The present disclosure relates to the field of orthopedic surgery, and more particularly to interbone fixation and fusion devices, and even more particularly, to intraarticular facet joint fixation and fusion devices.

BACKGROUND

The intervertebral discs of the human spine are prone to degeneration. In particular, the intervertebral discs located in highly mobile regions of the spine are disproportionately prone to degeneration, primarily due to overt and covert trauma to the tissue that occurs in the course of repetitive activities. Such trauma tends to disrupt the internal architecture of the disc, and the eventual collapse of the disc space. The resultant mechanical and/or chemical irritation of the surrounding neural elements, such as the spinal cord and nerves, may cause pain, inflammation, and varying degrees of osteoarthritis and attendant disability. Additionally, the loss of disc space height relaxes tension on the longitudinal spinal ligaments, thereby contributing to varying degrees of spinal instability, further exacerbating the degenerative change.

Various treatments have been developed to treat such intervertebral disc degeneration. Many of these treatments involve the fusion of adjacent vertebra in order to limit their ability to move independently from each other, as such independent movement tends to exacerbate the degeneration of the interposed disc and associated facet joints. These prior spinal fusion operations often involve either the passive grafting of bone between the surfaces of proximate articular processes in a facet joint that is denuded of synovium, or they involve the mechanical fixation of the facet joint with a simple screw.

These prior treatments, while fairly adequate for their purpose, suffer from a number of drawbacks. For example, operations that involve the passive grafting of bone require additional instrumented fixation of the spine to prevent dislodgement of the bone grafts from between the articular surfaces of the joint. Operations involving the mechanical fixation with a simple screw are largely adjunctive, that is, the screw alone is not sufficient as a means for fixing the facet joint. The long term success of this procedure is usually dependent upon bony union occurring elsewhere between the adjacent vertebral elements being fused, i.e., interbody or intertransverse posterolateral fusions.

Thus, there is a long felt need for a facet fixation device that can be utilized either directly or in a stand-alone facet fusion procedure or as an adjunctive fixator to be utilized when other forms of spinal fusion are employed, e.g., as back up for an anterior fusion. There is also a long felt need for such a device that may be deployed radiographically or through endoscopically assisted minimally invasive approaches, and that such a device both stabilize the facet joint and facilitate fusion of the joint.

SUMMARY

According to aspects illustrated herein, there is provided an expandable facet joint fixation device, comprising a first collar, a central shaft including a first end and a second end, the first end rotatably connected to the first collar, a second collar including a radially inward facing surface, the second collar concentrically arranged around the central shaft, and one or more expandable members, each of the one or more expandable members including a first arm hingedly connected to the first collar, a second arm hingedly connected to the second collar, the second arm hingedly connected to the first arm, wherein when the second collar is displaced in a first axial direction relative to the first collar, the one or more expandable members displace radially outward in a first radial direction.

According to aspects illustrated herein, there is provided an expandable joint fixation device, comprising an expansion cage, including a first collar, a second collar having a radially inward facing surface with interior threading, and one or more expandable members, and a central shaft extending through the second collar, the central shaft including a first end rotatably connected to the first collar, and a radially outward facing surface having exterior threading, the exterior threading being threadably engaged with the interior threading, and wherein when the second collar is displaced in a first axial direction relative to the first collar, the one or more expandable members displace radially outward in a first radial direction.

According to aspects illustrated herein, there is provided an expandable joint fixation device, comprising an expansion cage, including a first collar, a second collar having a radially inward facing surface with interior threading, and one or more expandable members, each of the one or more expandable members hingedly connected to the first and second collars, and a central shaft extending through the second collar, the central shaft being hollow and including a first end rotatably connected to the first collar, a radially outward facing surface having exterior threading threadably engaged with the interior threading, and one or more holes, wherein when the central shaft is rotated in a first circumferential direction, relative to the second collar, the second collar is displaced in a first axial direction relative to the first collar and the one or more expandable members displace radially outward in a first radial direction, and when the central shaft is rotated in a second circumferential direction, opposite the first circumferential direction, relative to the second collar, the second collar is displaced in a second axial direction, opposite the first axial direction, relative to the first collar and the one or more expandable members displace radially inward in a second radial direction, opposite the first radial direction.

The present disclosure broadly discloses an expandable device for fixating the position of proximate bone elements of the human cervical and lumbar spine to facilitate intra facet fusion and long term stability by first deploying the device into intra facet position and simultaneously rotating and expanding the device thereby creating a cavity in the bony interspace which can receive biologic products, and then detaching the expanded device in situ to foster bony fusion and long term spinal stability.

The present disclosure includes an expandable facet joint fixation device or device for fixing the positions of proximate bone elements, which is particularly adapted for the fixation of proximate articular processes in a facet joint. The device broadly comprises an interbone implant adapted to be implanted between suitably prepared proximate bone elements.

The expandable facet joint fixation device may comprises a central externally threaded shaft onto which are attached linkage arms connected to proximal and distal collars. The distal collar is fixed to the distal end of the central shaft, but permits independent rotation of the shaft within the distal collar. The proximal collar is threaded such that when the central threaded shaft is turned in a first circumferential direction, the two collars approach each other and when the central threaded shaft is turned in a second circumferential direction the two collars move away from each other.

Hinged arms are attached to each of the collars, which can bend outward when the proximal and distal collars are brought closer in proximity. Thus, when the central shaft is turned in a first circumferential direction and the proximal collar advances toward the distal collar, the arms are deployed radially outward, and when the central shaft is turned in a second circumferential direction, opposite the first circumferential direction, the hinged arms are drawn radially inward until they lie flush with or flat against the central shaft.

In some embodiments, the hinge of each arm is equidistant between the two collars; however, the hinge point can be varied such that it is not equidistant between the two collars. In some embodiments, the expandable facet joint fixation device comprises a plurality of arms. In some embodiments, the expandable facet joint fixation device comprises four hinged and deployable arms that deploy symmetrically when actuated.

In some embodiments, the expandable facet joint fixation device may comprise a retractable and rotatable sleeve that engages an outer collar attached to the arms, but does not impede independent rotation of the centrally threaded shaft or movement of the proximal collar. In this fashion, the entire device can be rotated while being incrementally expanded by simultaneous rotation of the central threaded shaft.

In some embodiments, the method of implanting the expandable facet joint fixation device comprises accessing the facet joint by inserting a Kirschner wire (K-wire) therein under fluoroscopic guidance, sliding a cylindrical dilator over the K-wire, sliding a cylindrical guide with distal tangs that engage the joint space over the K-wire, thereby stabilizing the cylindrical guide, and removing the K-wire and cylindrical dilator, leaving the tang tip cylindrical guide in place. A drill is then placed along the cylindrical guide or tube and a cylindrical channel is drilled into the facet joint engaging proximate facies of both superior and inferior facet.

The drill is then removed from the cylindrical guide and the expandable facet joint fixation device is inserted. The expandable facet joint fixation device external sleeve is connected to an air drill used to insert K-wires. The outer sleeve is then rotated in a drill like fashion, which in turn rotates the outer proximal collar and attached arms, but not the internal collar which is advanced slowly and manually along the central threaded shaft, as said central threaded shaft is slowly rotated. In some embodiments, the arms and the central shaft are rotated at the same speed during cutting to maintain the distance between the proximal and distal collars. During expansion, the arms and the central shaft are rotated at different speeds to enable the arms to expand radially outward as they are simultaneously rotating and cutting.

As the internal collar is advanced the spinning arms deploy and carve a cavity in the softer surrounding bone. The rotation of the expandable facet joint fixation device is stopped just prior to full expansion so that final expansion can be used to tighten the facet capsule and fixate the device. The central threaded shaft is then disconnected from the device and removed. Bone putty or other biologic material is then slid inside the outer sleeve and pressed into the device, completing the fusion. The outer sleeve is then attached and removed leaving the device and fusion material contained entirely within the now stabilized facet joint.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIGS. 4-10 show elevational views of a facet joint and the expandable facet joint fixation device being implanted therein;

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be appreciated that facet joints are a set of synovial, plane joints between the articular processes of two adjacent vertebrae. There are two facet joints in each spinal motion segment and each facet joint is innervated by the recurrent meningeal nerves.

By "non-rotatably connected" elements, we mean that: the elements are connected so that whenever one of the elements rotate, all the elements rotate; and relative rotation between the elements is not possible. Radial and/or axial movement of non-rotatably connected elements with respect to each other is possible, but not required. By "rotatably connected" elements, we mean that the elements are rotatable with respect to each other.

Figure 1A:
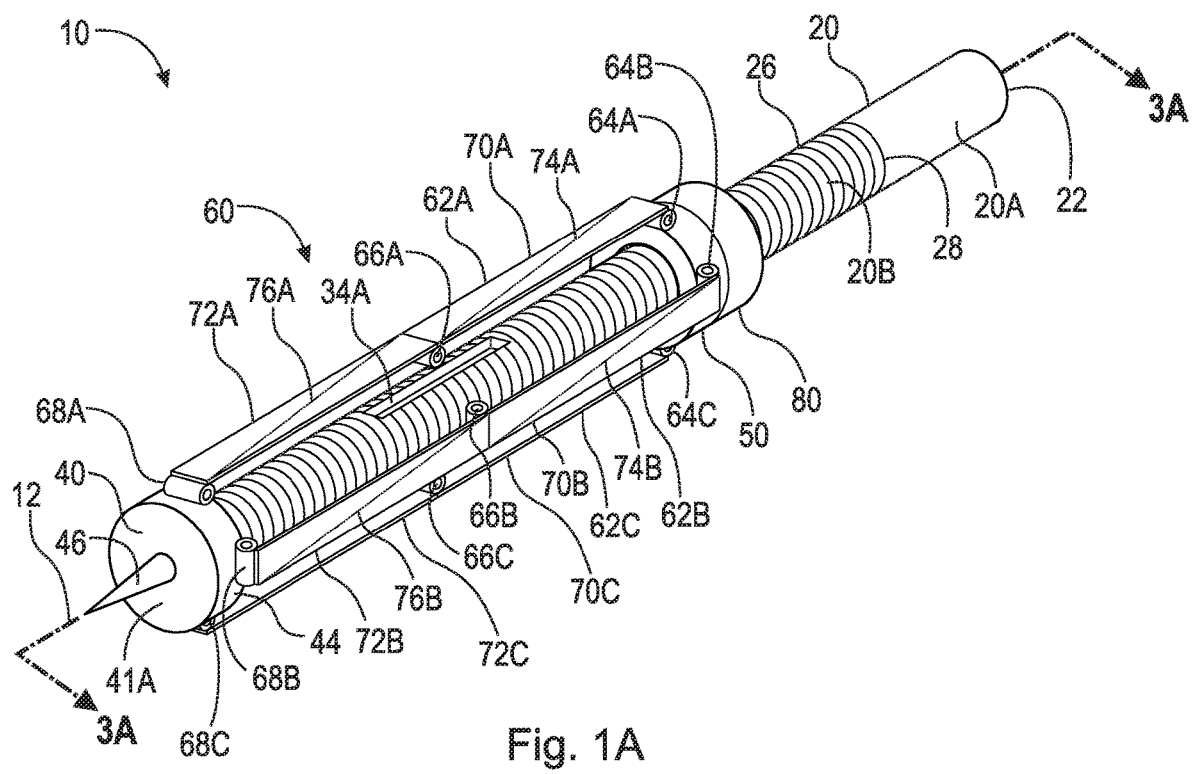
FIG. 1A is a perspective view of an expandable facet joint fixation device in an unexpanded state.
Figure 1B:
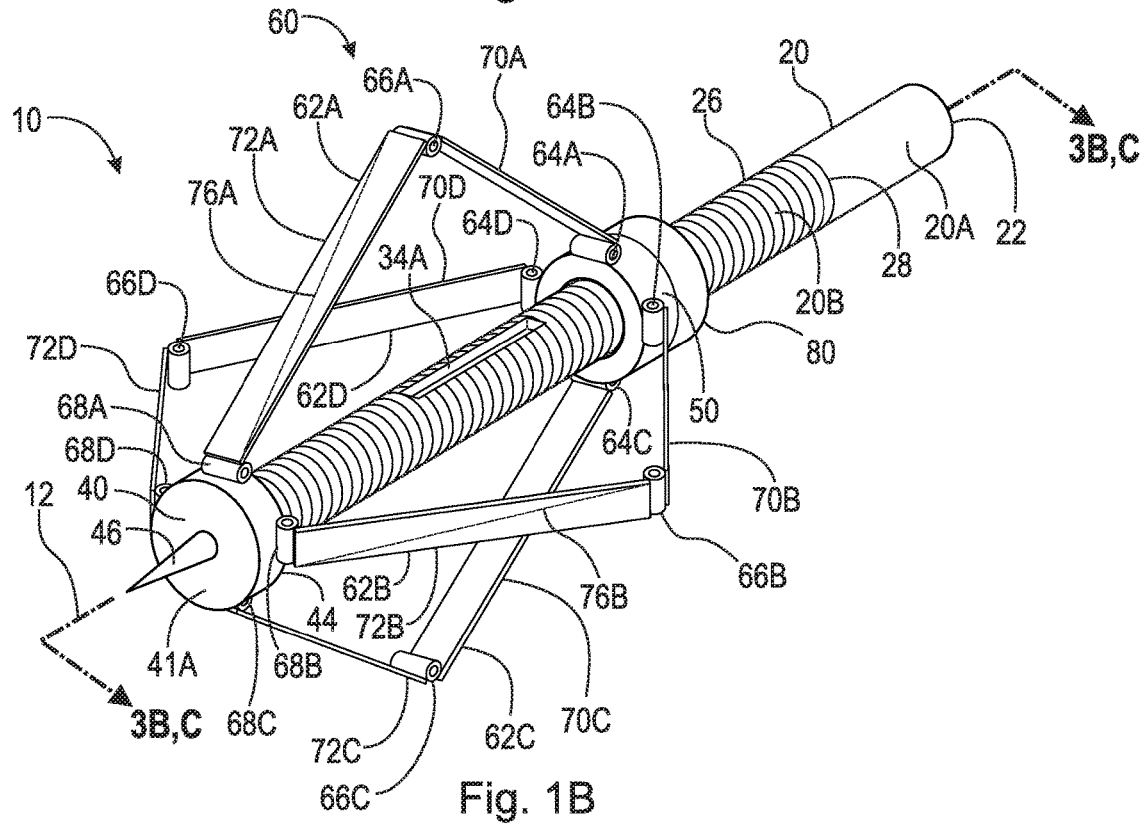
FIG. 1B is a perspective view of the expandable facet joint fixation device shown in FIG. 1A in a first expanded state.
Figure 2:
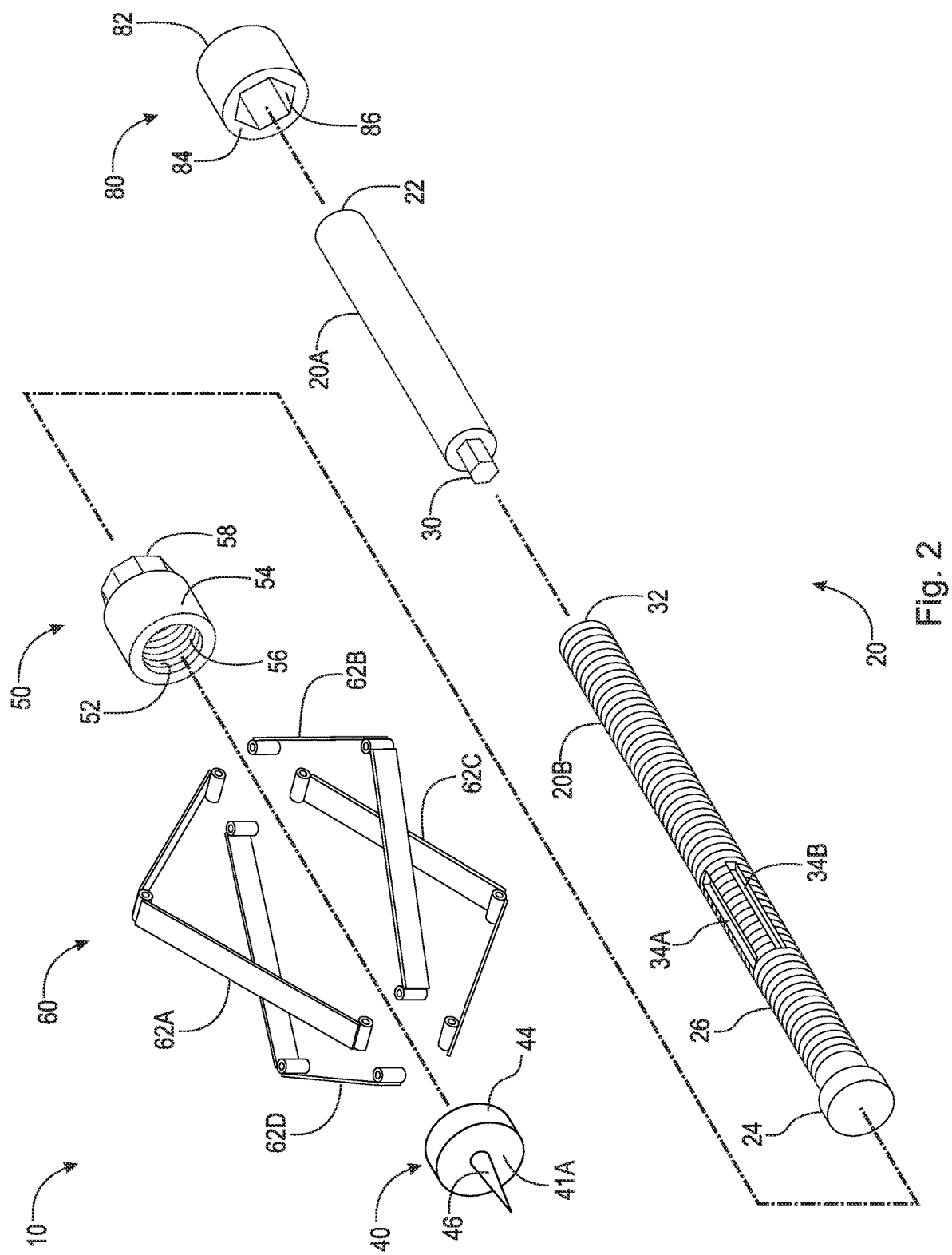
FIG. 2 is an exploded view of the expandable facet joint fixation device shown in FIG. 1A.
Figure 3A:
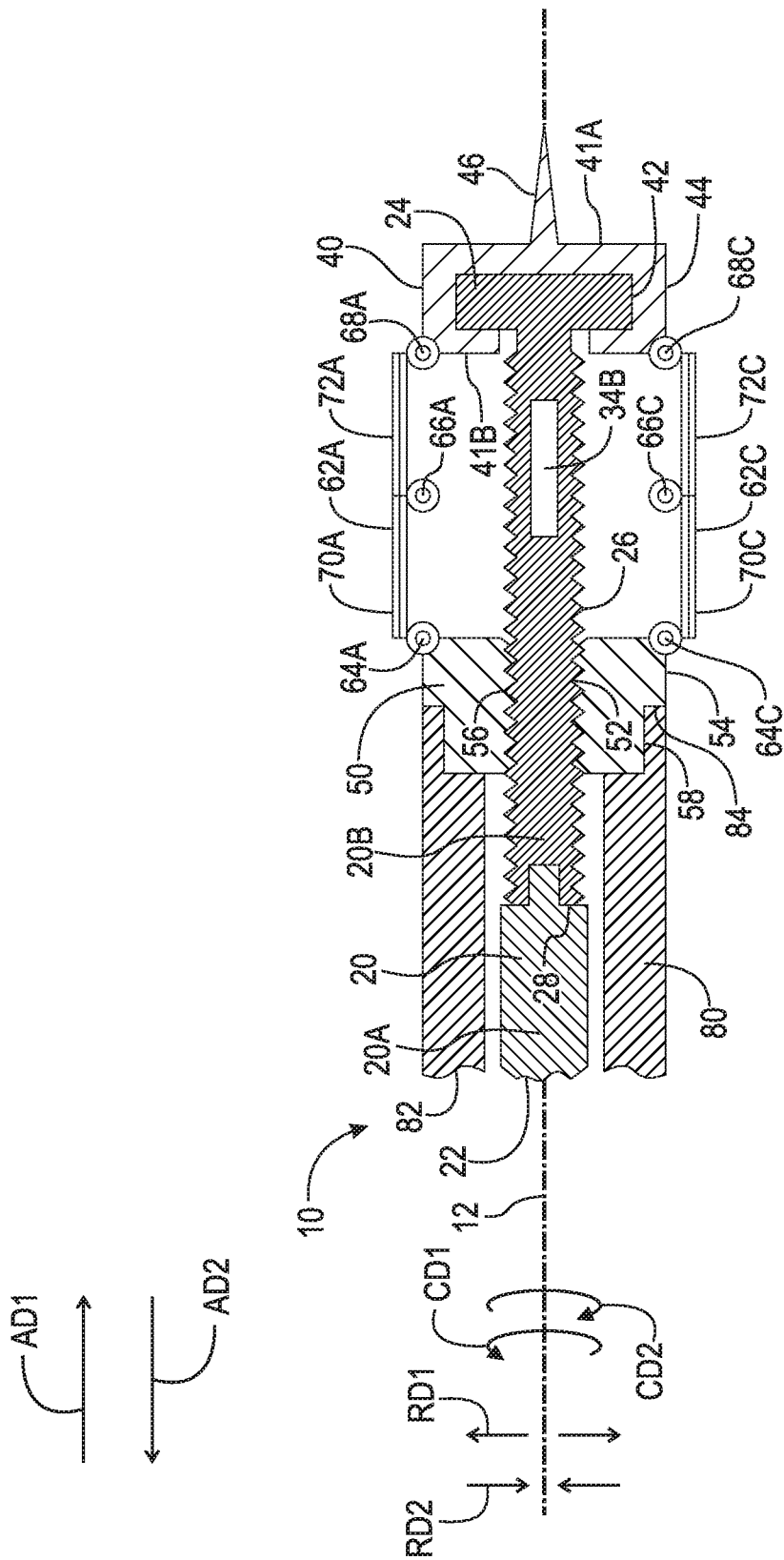
FIG. 3A is a cross-sectional view of the expandable facet joint fixation device taken generally along line 3A-3A in FIG. 1A in the unexpanded state.
Figure 3B:
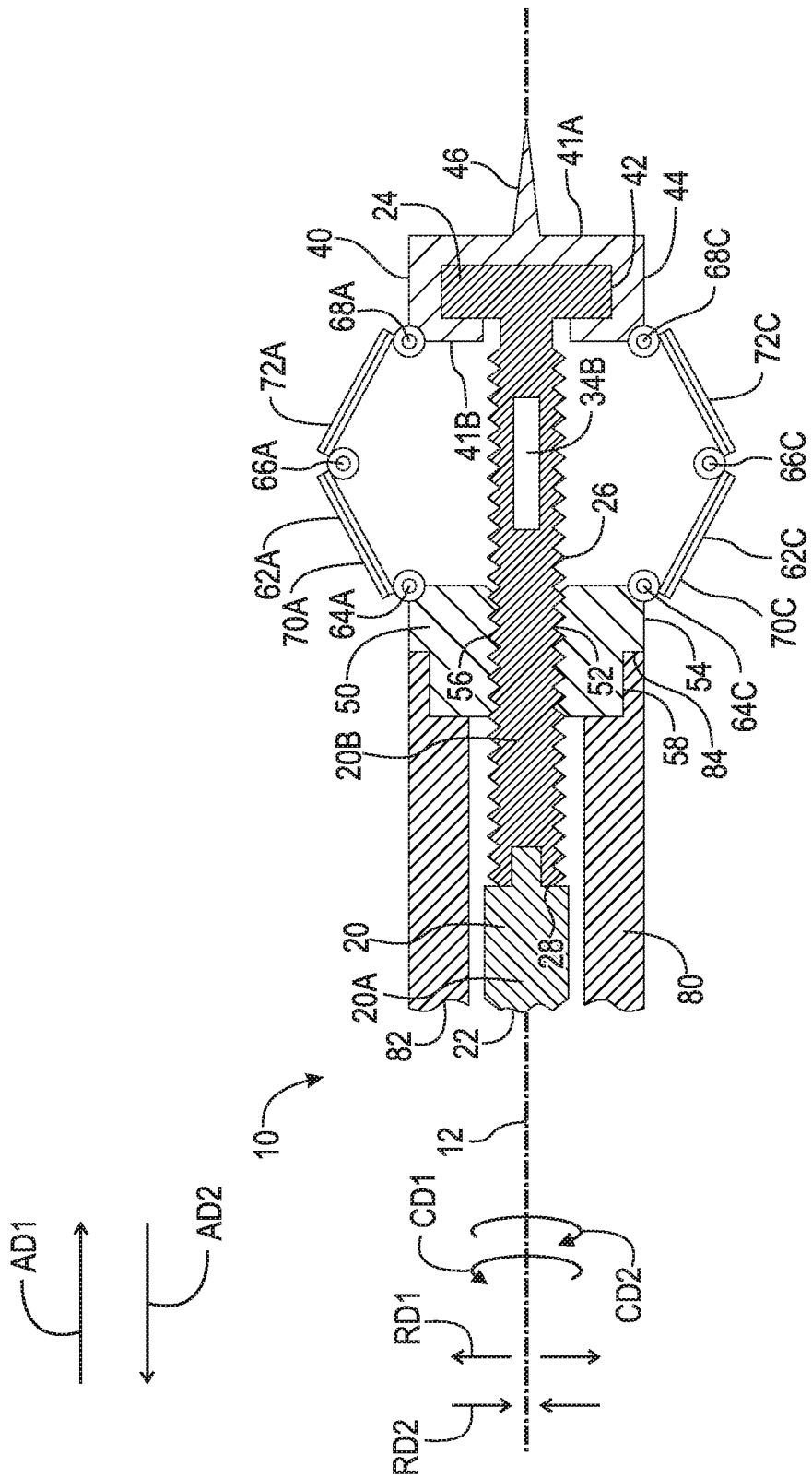
FIG. 3B is a cross-sectional view of the expandable facet joint fixation device taken generally along line 3B-3B in FIG. 1B in the first expanded state.
Figure 3C:
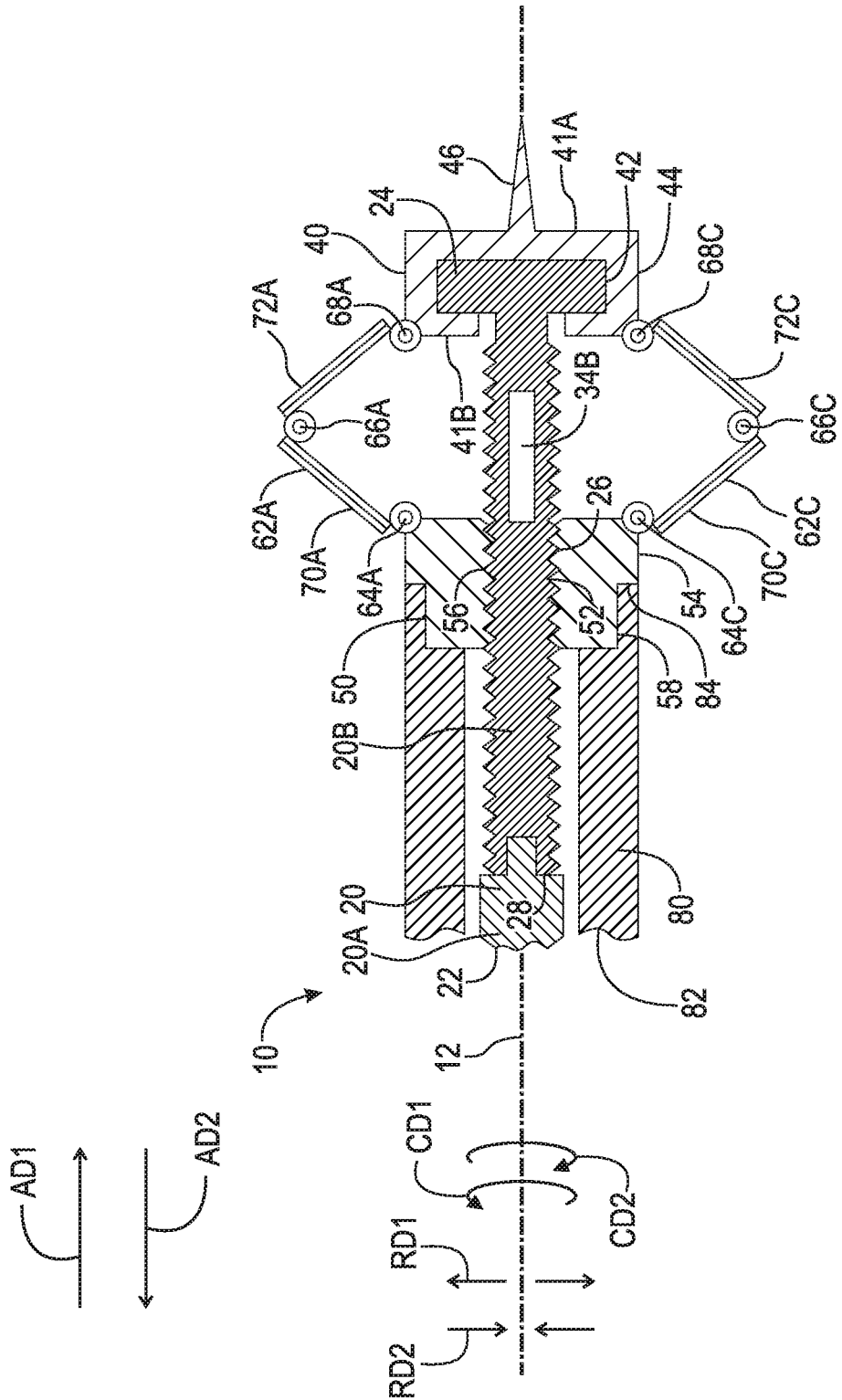
FIG. 3C is a cross-sectional view of the expandable facet joint fixation device taken generally along line 3C-3C in FIG. 1B in a second expanded state.

Referring now to the figures, FIG. 1A is a perspective view of expandable facet joint fixation device 10 in an unexpanded state. FIG. 1B is a perspective view of expandable facet joint fixation device 10 in a first expanded state. FIG. 2 is an exploded view of expandable facet joint fixation device 10. FIG. 3A is a cross-sectional view of expandable facet joint fixation device 10 taken generally along line 3A-3A in FIG. 1A in the unexpanded state. FIG. 3B is a cross-sectional view of expandable facet joint fixation device 10 taken generally along line 3B-3B in FIG. 1B in the first expanded state. FIG. 3C is a cross-sectional view of expandable facet joint fixation device 10 taken generally along line 3C-3C in FIG. 1B in a second expanded state. Expandable facet joint fixation device 10 generally comprises central shaft 20, collar 40, collar 50, and expansion cage 60. The following description should be read in view of FIGS. 1A-3C.

Central shaft 20 comprises end 22, end 24, and radially outward facing surface 25. Radially outward facing surface 25 comprises threading 26. Central shaft 20 is arranged to be separated into portions 20A and 20B at break plane 28. Portion 20B of central shaft 20 is arranged to engage collars 40 and 50. Portion 20B comprises threading 26 at least partially thereon. In some embodiments, threading 26 extends completely over portion 20B. In some embodiments, central shaft 20 is a singular shaft comprising threading 26 at least partially thereon. End 24 is rotatably connected to collar 40. Threading 26 engages collar 50 to expand and contract expansion cage 60, as will be discussed in greater detail below. Portion 20A is arranged to be removably and non-rotatably connected to portion 20B at break plane 28. In some embodiments, portion 20A comprises wrench or a key 30 (e.g., Allen wrench or hex key, square key, etc.), which engages socket or head 32 (hexagonal hole, square hole, etc.) of portion 20B, such that portion 20A and portion 20B are non-rotatably connected. In some embodiments, portion 20A comprises external threading and portion 20B comprises internal threading, and portion 20A screws into portion 20B. In some embodiments, portion 20B is a tube. In some embodiments, portion 20A comprises internal threading and portion 20B comprises external threading, and portion 20A screws onto portion 20B. In some embodiments, portion 20B is a hollow tube comprising holes 34A-C. Once portion 20A is removed from portion 20B, bone putty or bone fusion material can be pumped into portion 20B through socket 32, and then into the cavity created by expandable facet joint fixation device 10, as will be discussed in greater detail below. Holes 34A-C allow the bone putty pumped into portion 20B through socket 32 to flow into the cavity created by expandable facet joint fixation device 10. In some embodiments, portion 20B comprises one or more holes. In the embodiment shown in the figures, portion 20B comprises three holes 34A-C.

Collar 40 comprises surface 41A, surface 41B, hole 42, radially outward facing surface 44, and tip 46. Hole 42 extends from surface 41B in axial direction AD1 and is arranged to engage end 24 of central shaft 20, such that when connected, central shaft 20 is axially fixed but rotatable with respect to collar 40. As shown in FIGS. 3A-C, hole 42 comprises a flange that extends radially inward in radial direction RD2 to enclose a flange arranged on end 24. It should be appreciated, however, that any suitable method of rotatably connecting central shaft 20 to collar 40 may be used. Tip 46 extends from surface 41A in axial direction AD1. Tip 46 is arranged to engage a bone, joint, or facet joint, to provide an anchor for skeletal traction. Tip 46 may, for example, engage cartilage in the facet joint, as will be discussed in greater detail below. In the embodiment shown, collar 40, specifically, radially outward facing surface 44, is cylindrical with a circular cross-section. However, it should be appreciated that radially outward facing surface 44 may comprise any geometry (e.g., square, rectangular, ovular, trapezoidal, etc.) suitable for securing hinges 68A-D, as will be discussed in greater detail below.

Collar 50 is generally an annular ring comprising radially inward facing surface 52 and radially outward facing surface 54. Radially inward facing surface 52 comprises threading 56 which engages threading 26 of central shaft 20. Threading 56 and threading 26 is engaged such that, for example, when central shaft 20 is rotated in circumferential direction CD1 relative to collar 50, collar 50 displaces in axial direction AD1 relative to collar 40, and expansion cage 60 expands in radial direction RD1. When central shaft 20 is rotated in circumferential direction CD2 relative to collar 50, collar 50 displaces in axial direction AD2 relative to collar 40, and expansion cage 60 contracts in radial direction RD2. It should be appreciated that threading 56 and threading 26 may be oppositely engaged such that, for example, when central shaft 20 is rotated in circumferential direction CD2 relative to collar 50, collar 50 displaces in axial direction AD1 relative to collar 40, and expansion cage 60 expands in radial direction RD1. When central shaft 20 is rotated in circumferential direction CD1 relative to collar 50, collar 50 displaces in axial direction AD2 relative to collar 40, and expansion cage 60 contracts in radial direction RD2. In some embodiments, radially outward facing surface 54 comprises engaging component 58 to be non-rotatable connected to outer sleeve 80, as will be discussed in greater detail below. For example, engaging component 58 may be a hex head or have a protrusion that outer sleeve 80 can slide over, similar to a socket and bolt. It should be appreciated, however, that any engaging component suitable for non-rotatable connection to an outer sleeve may be used. In the embodiment shown, collar 50, specifically, radially outward facing surface 54, is cylindrical with a circular cross-section. However, it should be appreciated that radially outward facing surface 54 may comprise any geometry (e.g., square, rectangular, ovular, trapezoidal, etc.) suitable for securing hinges 64A-D, as will be discussed in greater detail below. In some embodiments, expandable facet joint fixation device 10 may include an intermediate collar arranged radially between collar 50 and central shaft 20, which allows collar 50 and expansion cage to rotate rapidly independent of central shaft 20 while maintaining the distance between collars 40 and 50. In some embodiments, a bearing is included between collar 50 and the intermediate collar.

Expansion cage 60 comprises a plurality of arms and hinges. In some embodiments, expansion cage 60 may comprise one or more expandable members, with each expandable member including one or more hinges and one or more arms. In the embodiment shown, expansion cage 60 comprises expandable members 62A-D, as is discussed in greater detail below.

Expandable member 62A comprises hinge 64A, hinge 66A, hinge 68A, arm 70A, and arm 72A. Arm 70A is hingedly connected to collar 50 via hinge 64A. Arm 72A is hingedly connected to arm 70A via hinge 66A. Arm 72A is hingedly connected to collar 40 via hinge 68A. As collar 50 is displaced in axial direction AD1 relative to collar 40 (i.e., the distance between collars 40 and 50 decreases), arm 70A, arm 72A, and hinge 66A expand radially outward in radial direction RD1. As collar 50 is displaced in axial direction AD2 relative to collar 40 (i.e., the distance between collars 40 and 50 increases), arm 70A, arm 72A, and hinge 66A contract radially inward in radial direction RD2. In some embodiments, arms 70A and 72A comprise cutting surfaces 74A and 76A, respectively. As expandable facet joint fixation device 10, specifically expansion cage 60, is rotated about axis of rotation 12 in circumferential direction CD1 and/or CD2, cutting surfaces 74A and 76A cut into adjacent bone to create a cavity, as will be discussed in greater detail below.

Expandable member 62B comprises hinge 64B, hinge 66B, hinge 68B, arm 70B, and arm 72B. Arm 70B is hingedly connected to collar 50 via hinge 64B. Arm 72B is hingedly connected to arm 70B via hinge 66B. Arm 72B is hingedly connected to collar 40 via hinge 68B. As collar 50 is displaced in axial direction AD1 relative to collar 40 (i.e., the distance between collars 40 and 50 decreases), arm 70B, arm 72B, and hinge 66B expand radially outward in radial direction RD1. As collar 50 is displaced in axial direction AD2 relative to collar 40 (i.e., the distance between collars 40 and 50 increases), arm 70B, arm 72B, and hinge 66B contract radially inward in radial direction RD2. In some embodiments, arms 70B and 72B comprise cutting surfaces 74B and 76B, respectively. As expandable facet joint fixation device 10, specifically expansion cage 60, is rotated about axis of rotation 12 in circumferential direction CD1 and/or CD2, cutting surfaces 74B and 76B cut into adjacent bone to create a cavity, as will be discussed in greater detail below.

Expandable member 62C comprises hinge 64C, hinge 66C, hinge 68C, arm 70C, and arm 72C. Arm 70C is hingedly connected to collar 50 via hinge 64C. Arm 72C is hingedly connected to arm 70C via hinge 66C. Arm 72C is hingedly connected to collar 40 via hinge 68C. As collar 50 is displaced in axial direction AD1 relative to collar 40 (i.e., the distance between collars 40 and 50 decreases), arm 70C, arm 72C, and hinge 66C expand radially outward in radial direction RD1. As collar 50 is displaced in axial direction AD2 relative to collar 40 (i.e., the distance between collars 40 and 50 increases), arm 70C, arm 72C, and hinge 66C contract radially inward in radial direction RD2. In some embodiments, arms 70C and 72C comprise cutting surfaces 74C and 76C, respectively. As expandable facet joint fixation device 10, specifically expansion cage 60, is rotated about axis of rotation 12 in circumferential direction CD1 and/or CD2, cutting surfaces 74C and 76C cut into adjacent bone to create a cavity, as will be discussed in greater detail below.

Expandable member 62D comprises hinge 64D, hinge 66D, hinge 68D, arm 70D, and arm 72D. Arm 70D is hingedly connected to collar 50 via hinge 64D. Arm 72D is hingedly connected to arm 70D via hinge 66D. Arm 72D is hingedly connected to collar 40 via hinge 68D. As collar 50 is displaced in axial direction AD1 relative to collar 40 (i.e., the distance between collars 40 and 50 decreases), arm 70D, arm 72D, and hinge 66D expand radially outward in radial direction RD1. As collar 50 is displaced in axial direction AD2 relative to collar 40 (i.e., the distance between collars 40 and 50 increases), arm 70D, arm 72D, and hinge 66D contract radially inward in radial direction RD2. In some embodiments, arms 70D and 72D comprise cutting surfaces 74D and 76D, respectively. As expandable facet joint fixation device 10, specifically expansion cage 60, is rotated about axis of rotation 12 in circumferential direction CD1 and/or CD2, cutting surfaces 74D and 76D cut into adjacent bone to create a cavity, as will be discussed in greater detail below.

Outer sleeve 80 comprises end 82, end 84, and socket 86. Outer sleeve 80 is arranged to removably and non-rotatably connect to collar 50. Specifically, socket 86 engages engaging component 58. As previously mentioned, as central shaft 20 is rotated relative to collar 50, the distance between collars 40 and 50 increase/decrease. As such, outer sleeve 80 allows the user to prevent collar 50 from rotating as central shaft 20 is being rotated (i.e., expansion mode). Additionally, the user can rotate both outer sleeve 80, and thus collar 50, and central shaft 20 at the same time and rotational speed to rotate expandable facet joint fixation device 10 (i.e., cutting mode). In cutting mode, a drill may be used to rotate both central shaft 20 and collar 50 at the same rotational speed, which allows expandable facet joint fixation device 10 to rotate about axis of rotation 12 without expansion cage 60 expanding or contracting (i.e., the distance between collars 40 and 50 remains constant). This can be envisioned by using a drill and a drill attachment which non-rotatably connects central shaft 20 and outer sleeve 80. In expansion mode, outer sleeve 80 and collar 50 are held in place (i.e., prevented from rotating) while central shaft 20 is rotated to expand expansion cage 60 in radial direction RIM. Once expansion cage 60 is expanded such that respective arms of expandable members 62A-D are tightly pressed against adjacent articular processes, the drill and drill attachment are again used to non-rotatably connect central shaft 20 and outer sleeve 80 and rotate expandable facet joint fixation device 10. Once a cavity of a desired size is formed in the facet joint, central shaft 20 is rotated with respect to outer sleeve 80 such that expandable members 62A-D are pressed tightly against the adjacent articular processes, and outer sleeve 80 is removed from collar 50. Portion 20A is then removed from portion 20B, and bone putty or bony or biologic material is then injected into portion 20B through socket 32. The bone putty flows out of holes 34A-C and to adjacent articular processes and hence can foster interbody fusion. In an example embodiment, bony growth and permanent fixation may be achieved with hardenable materials such as bone putty or methyl methacrylate (MMA) as is known to those having ordinary skill in the art. It should be appreciated that to expand expansion cage 60 in radial direction RIM while also cutting (i.e., rotating expansion cage 60), both outer sleeve 80 (and thus collar 50) and central shaft 20 are rotated but at different rotational speeds to allow the distance between collars 40 and 50 to decrease. For example, central shaft 20 and collar 50 rotate in the same circumferential direction with central shaft 20 being rotated at a greater rotational speed than that of collar 50.

FIGS. 4-10 show elevational views of facet joint 112 and expandable facet joint fixation device 10 being implanted therein. Vertebra 100 comprises spinous process 102, inferior articular process 104, superior articular process 108, and vertebral foramen 110. Facet joint 112 is formed between inferior articular process 104 and superior articular process 108.

Figure 5:
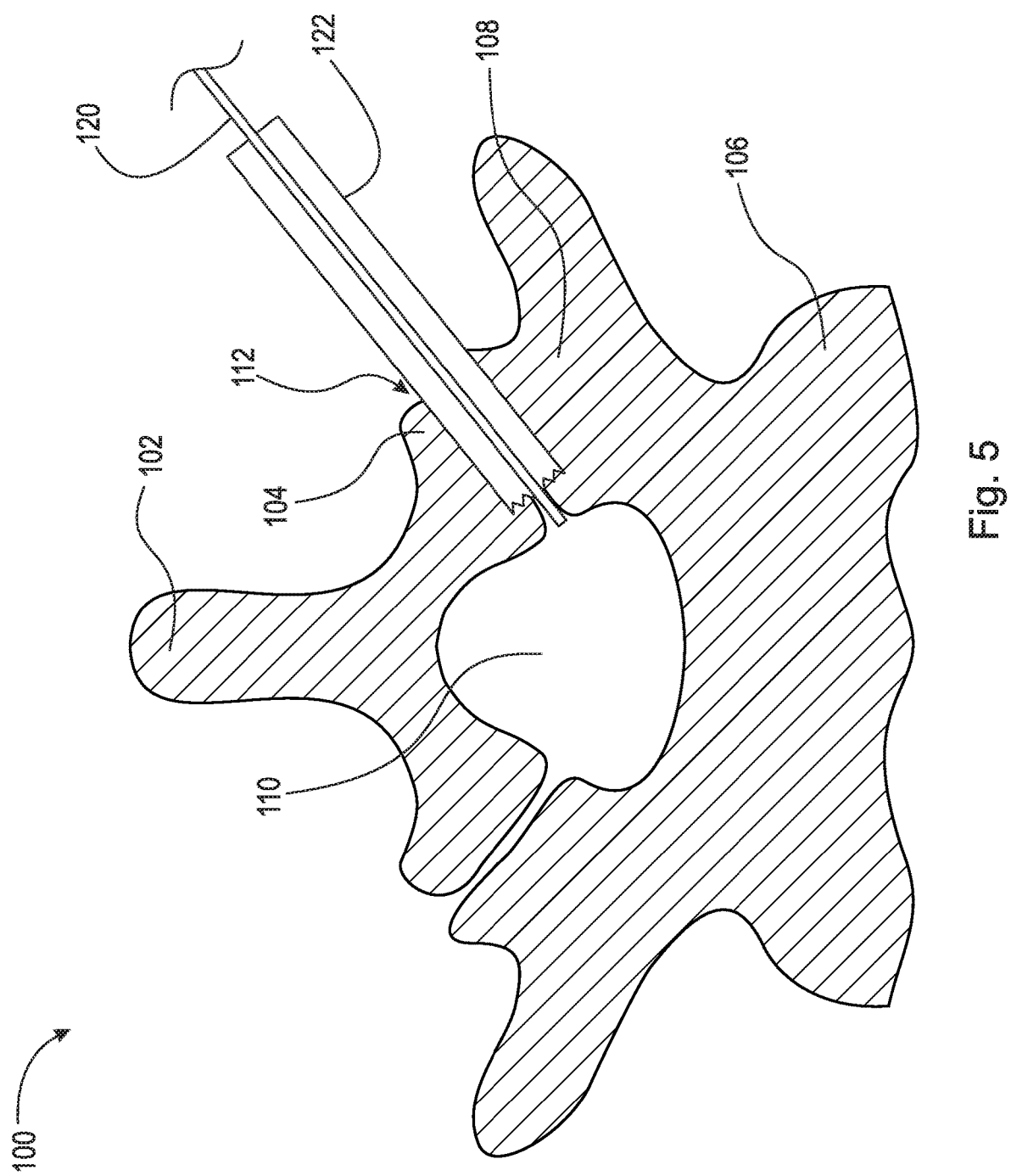
Figure 6:
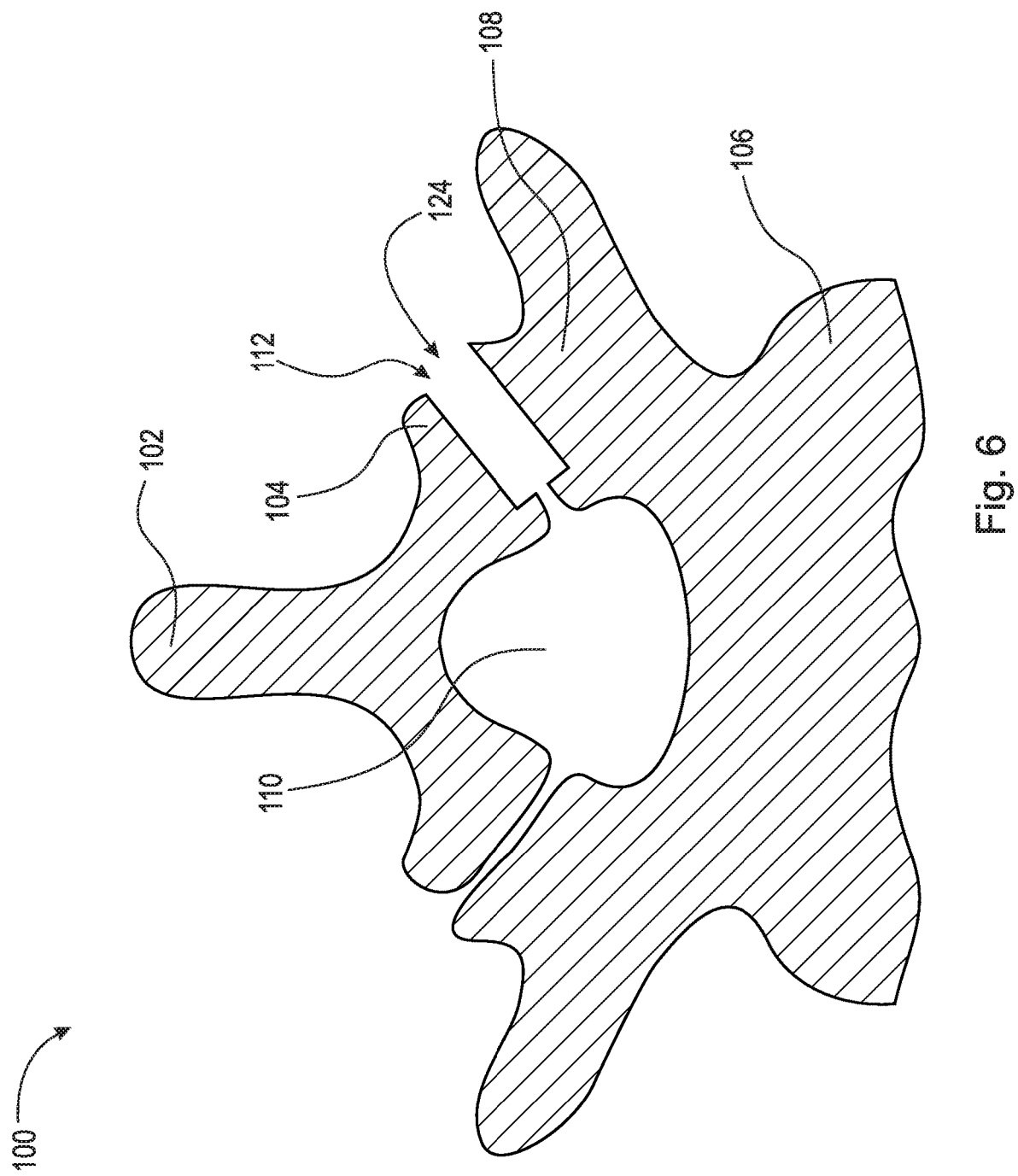
Figure 7:
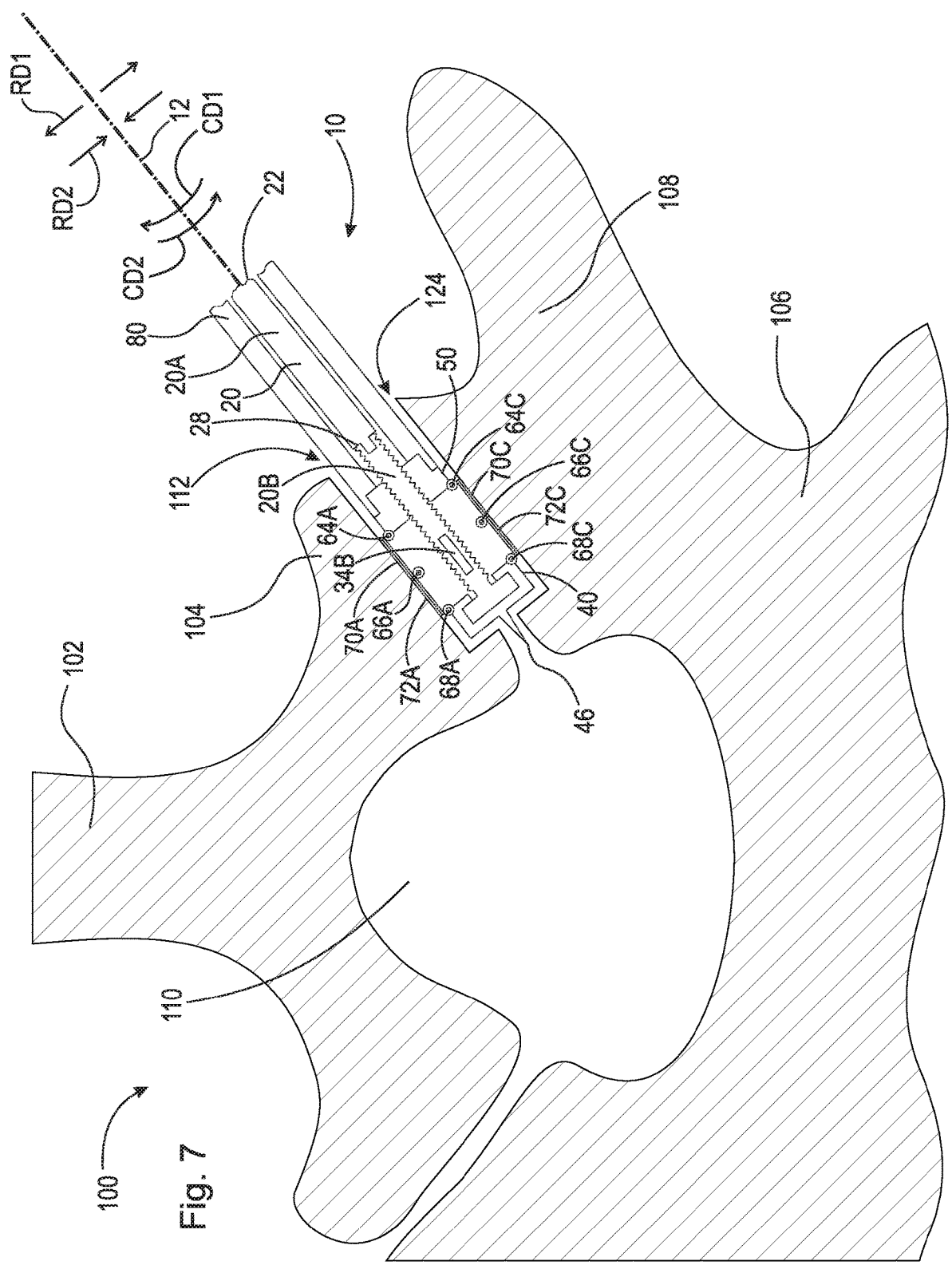
Figure 8:
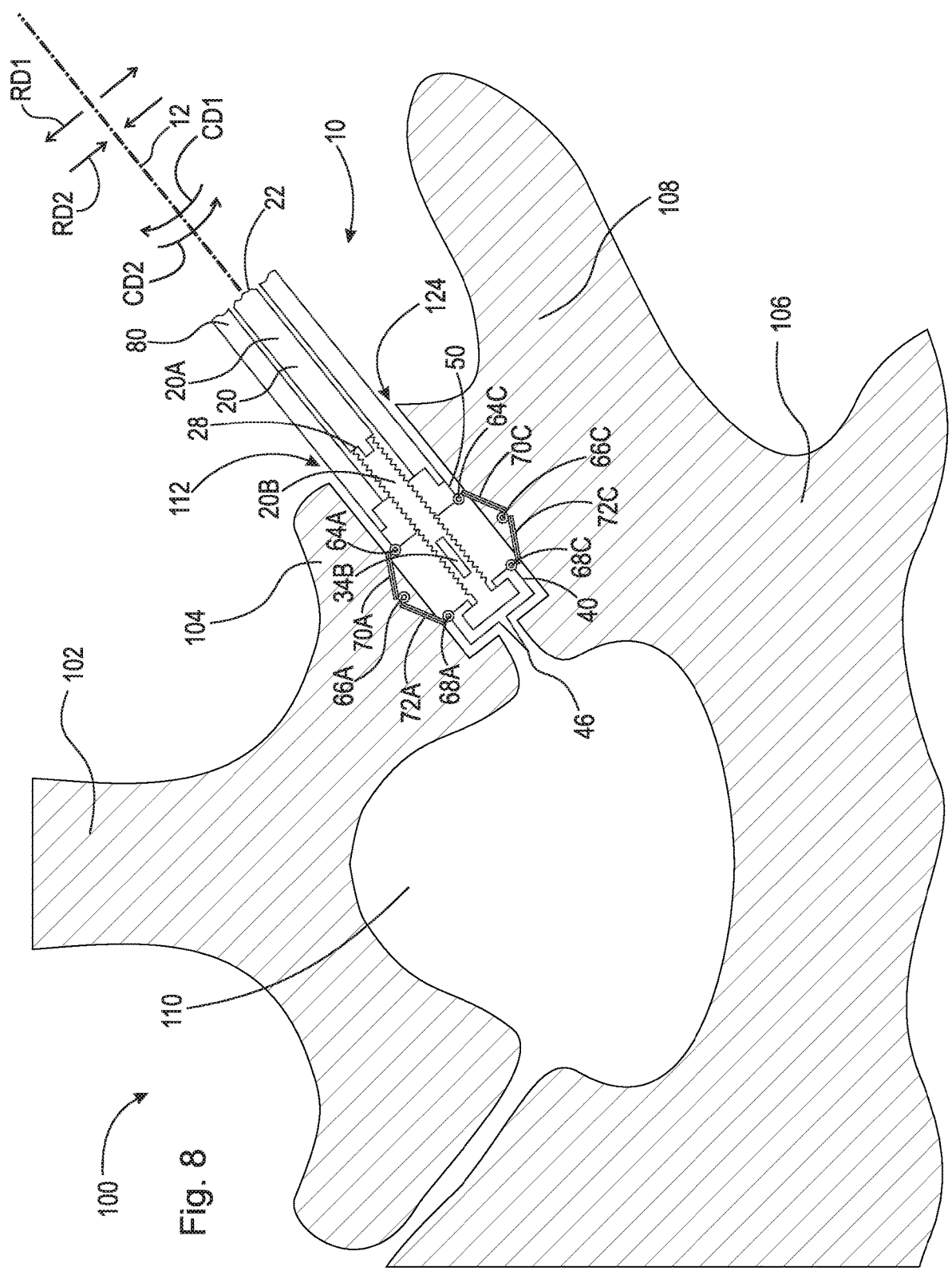
Figure 9:
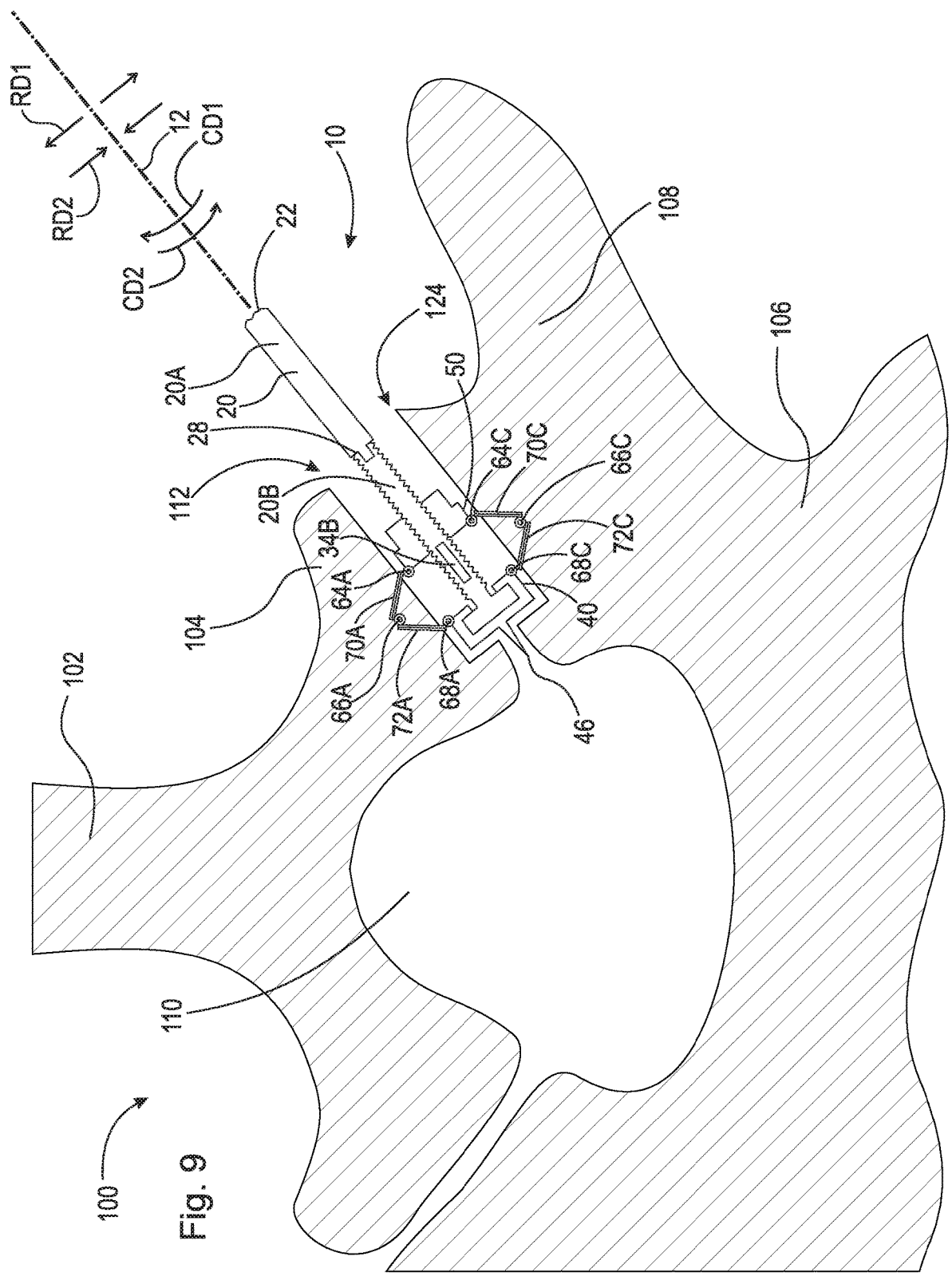

As shown in FIG. 4, K-wire 120 is inserted into facet joint 112. Specifically, K-wire 120 is inserted into the cartilage in facet joint 112 providing a guide for drill 122. Drill 122 is arranged on K-wire 120 and directed toward facet joint 112. As shown in FIG. 5, drill 122 is advanced into facet joint 112 to form a hole. As shown in FIG. 6, hole 124 is formed in facet joint 112. The diameter of hole 124 should be large enough such that expandable facet joint fixation device 10 can be inserted therein in the unexpanded state. FIG. 7 shows expandable facet joint fixation device 10 in the unexpanded state inserted into hole 124. As shown, portion 20A is non-rotatably connected to portion 20B at break plane 28, and outer sleeve 80 is non-rotatably connected to collar 50. In FIG. 8, expandable facet joint fixation device 10 is rotated rapidly. Specifically, expansion cage 60 is rotated rapidly to cut into adjacent articular processes. During or in between rotation, central shaft 20 is rotated with respect to collar 50 such that expansion members 62A-D expand radially outward allowing the cutting surfaces of the respective arms to cut into adjacent bone and continue to increase the size of the cavity. In some embodiments, during rapid rotation of expandable facet joint fixation device 10, central shaft 20 and outer sleeve 80 may be rotated at different rates to achieve the desired expansion or contraction of expansion cage 60. Once the desired expansion of expandable facet joint fixation device 10 is achieved, as shown in FIG. 9, rapid rotation is stopped. Further expansion of expandable facet joint fixation device 10 is carried out by rotating central shaft 20 relative to outer sleeve 80, which tightens facet capsule ligaments. Then outer sleeve 80 is removed from collar 50. As shown in FIG. 10, portion 20A is then disconnected from portion 20B. The remaining portion of expandable facet joint fixation device 10, i.e., collar 40, collar 50, expansion cage 60, and portion 20B is left in the cavity as an internal stabilizer in facet joint 112. Bone products can then be injected into socket 32, through portion 20B, and out of holes 34A-C to facilitate bone fusion. It should be appreciated that expandable facet joint fixation device 10 can be used for the fusion of any two adjacent bones, and that this disclosure should not be limited to only the fusion of adjacent articular processes at facet joints.

Figure 11A:
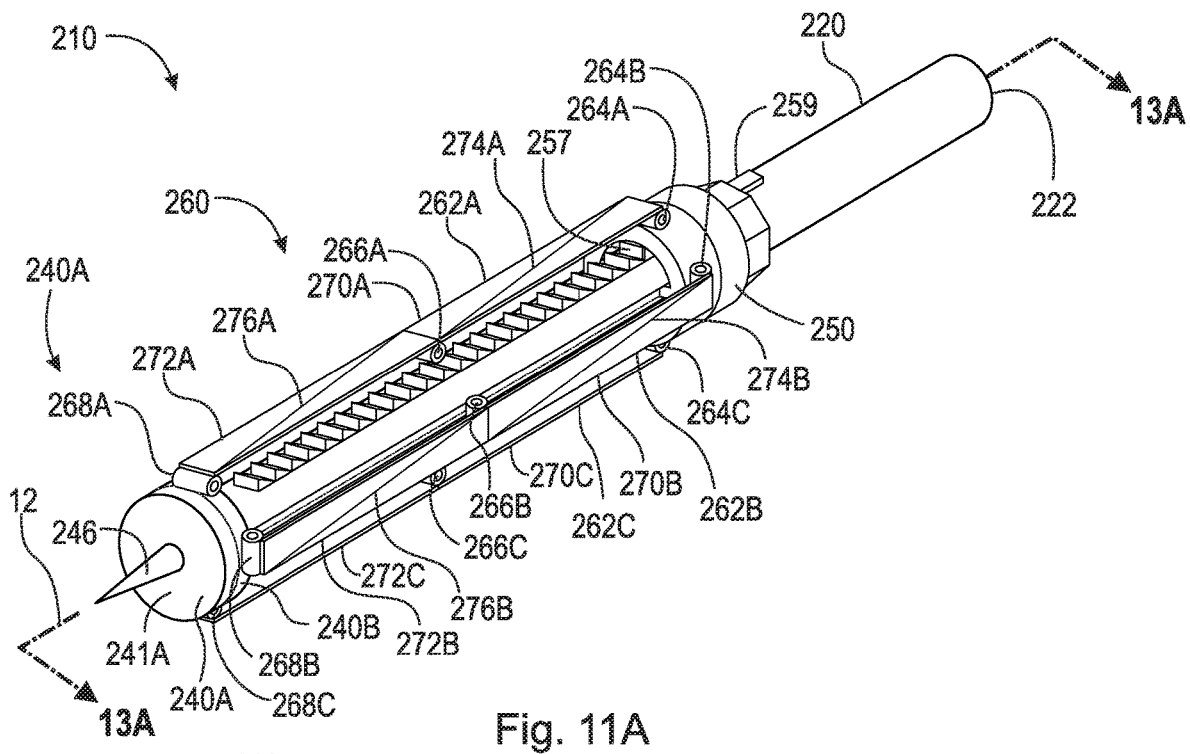
FIG. 11A is a perspective view of an expandable facet joint fixation device in an unexpanded state.
Figure 11B:
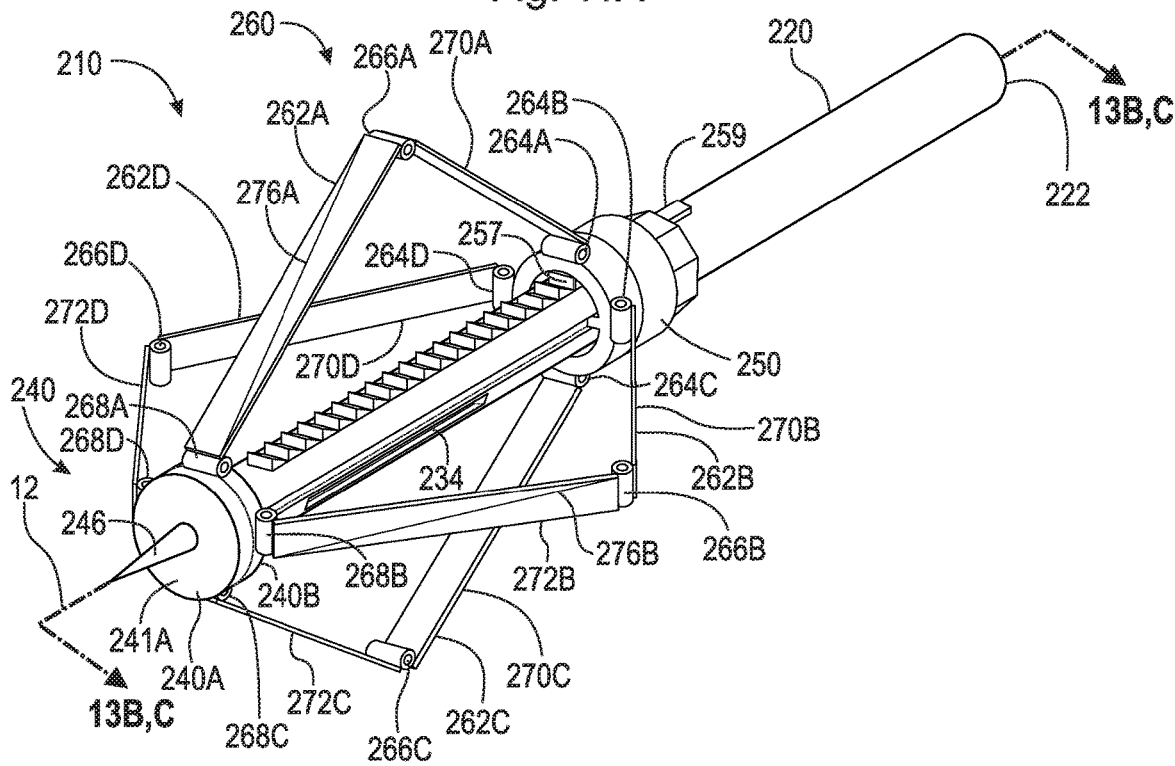
FIG. 11B is a perspective view of the expandable facet joint fixation device shown in FIG. 11A in a first expanded state.
Figure 12:
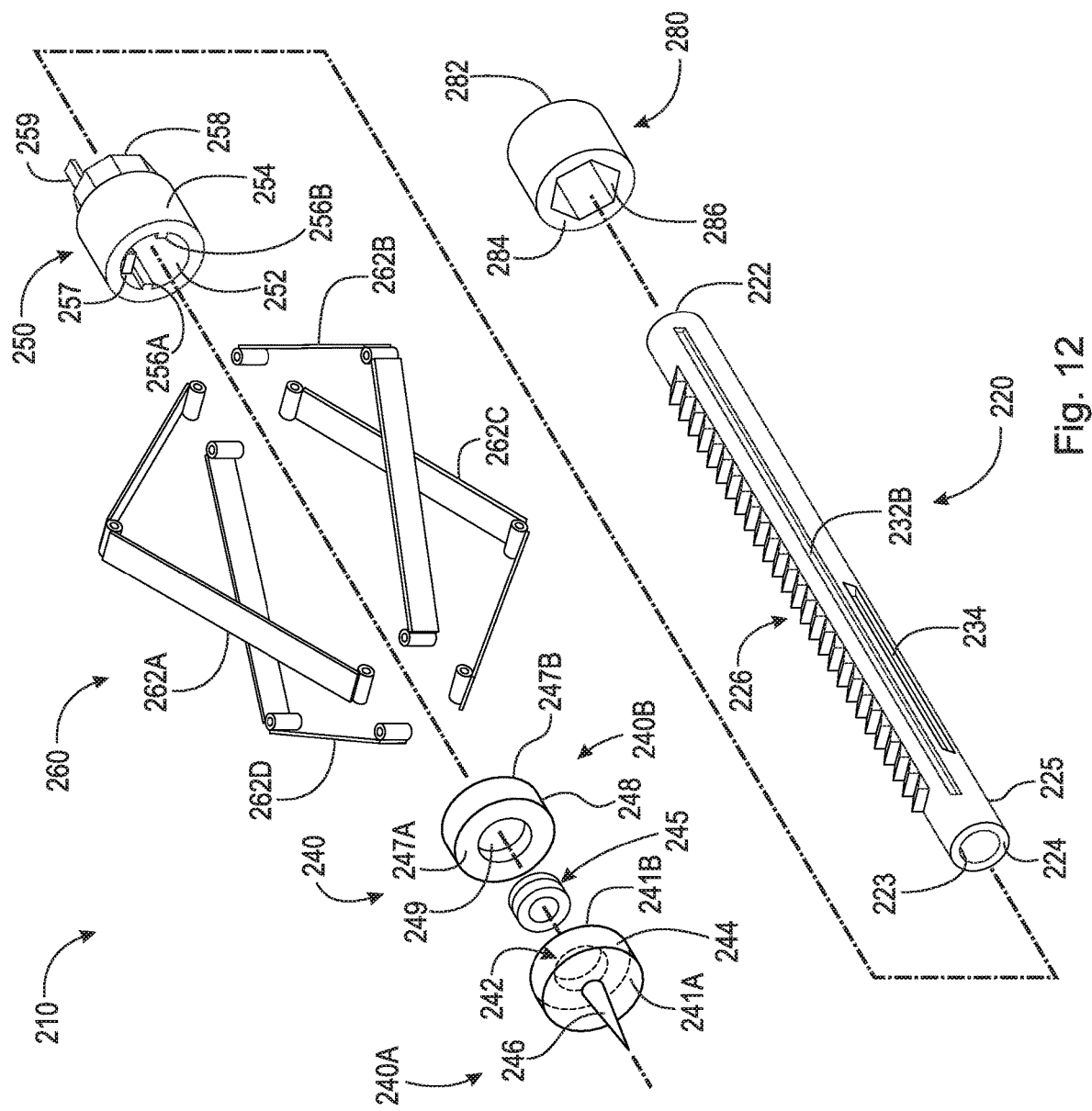
FIG. 12 is an exploded view of the expandable facet joint fixation device shown in FIG. 11A.
Figure 13A:
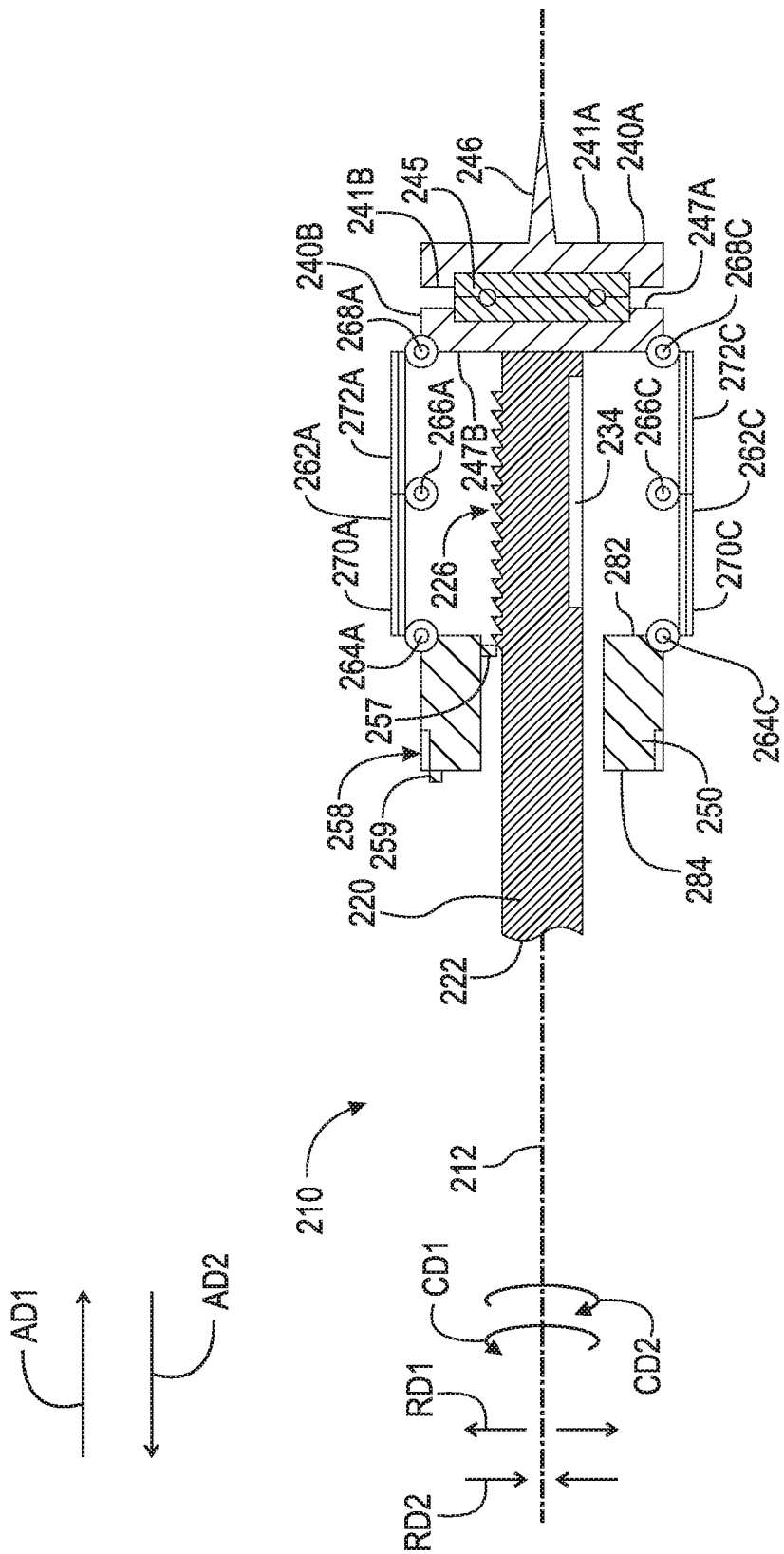
FIG. 13A is a cross-sectional view of the expandable facet joint fixation device taken generally along line 13A-13A in FIG. 11A in the unexpanded state.
Figure 13B:
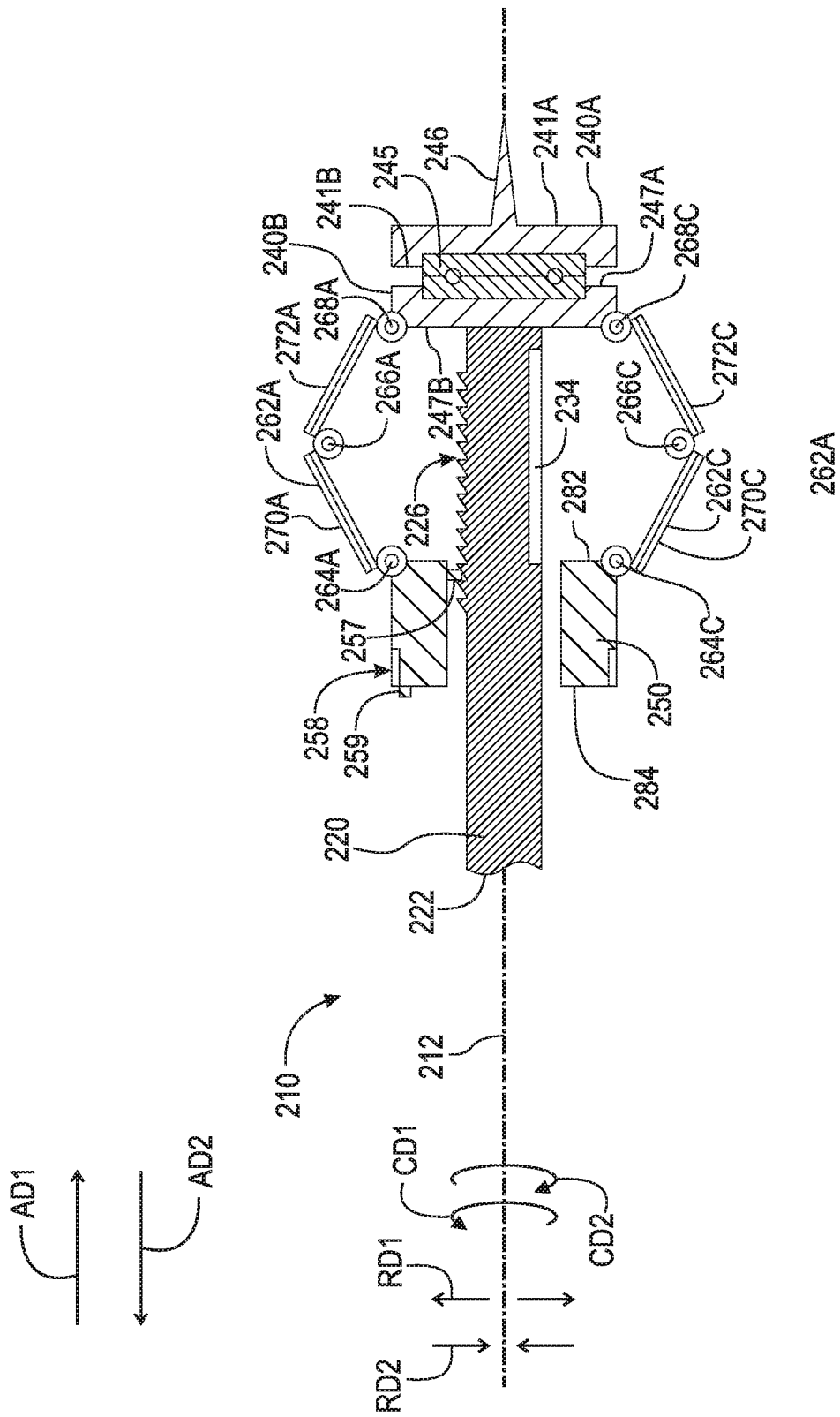
FIG. 13B is a cross-sectional view of the expandable facet joint fixation device taken generally along line 13B-13B in FIG. 11B in the first expanded state; and, FIG. 13C is a cross-sectional view of the expandable facet joint fixation device taken generally along line 13C-13C in FIG. 11B in a second expanded state.
Figure 13C:
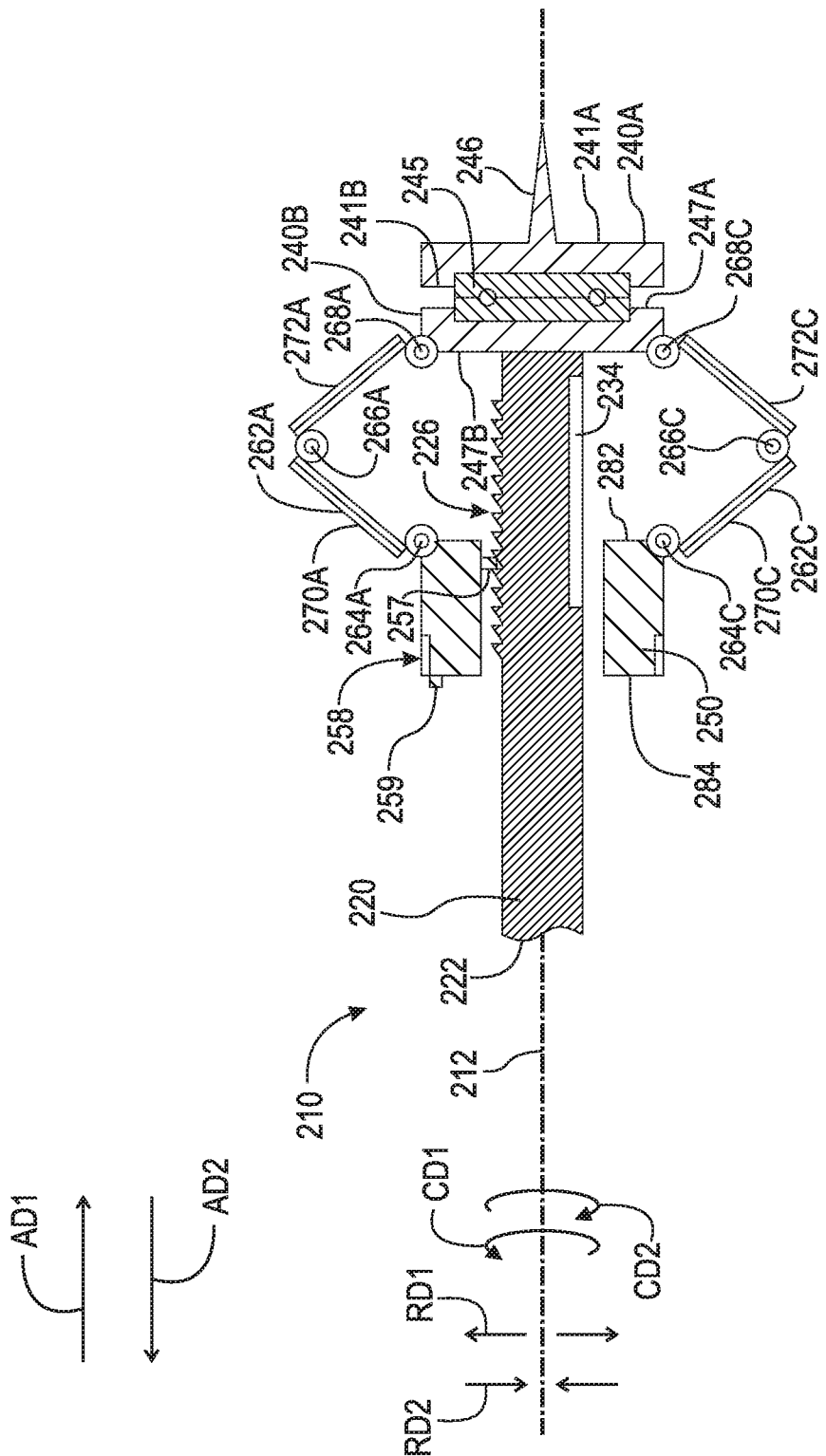

FIG. 11A is a perspective view of expandable facet joint fixation device 210 in an unexpanded state. FIG. 11B is a perspective view of expandable facet joint fixation device 210 in a first expanded state. FIG. 12 is an exploded view of expandable facet joint fixation device 210. FIG. 13A is a cross-sectional view of expandable facet joint fixation device 210 taken generally along line 13A-13A in FIG. 11A in the unexpanded state. FIG. 13B is a cross-sectional view of expandable facet joint fixation device 210 taken generally along line 13B-13B in FIG. 11B in the first expanded state. FIG. 13C is a cross-sectional view of expandable facet joint fixation device 210 taken generally along line 13C-13C in FIG. 11B in a second expanded state. Expandable facet joint fixation device 210 generally comprises central shaft 220, collar 240, collar 250, and expansion cage 260. The following description should be read in view of FIGS. 11A-13C.

Central shaft 220 is a hollow shaft comprising end 222, end 224, radially inward facing surface 223, and radially outward facing surface 225. Radially outward facing surface 225 comprises teeth 226. In some embodiments, central shaft 220 is arranged to be separated into portions at a break plane. Central shaft 220 is arranged to engage collars 240 and 250. Central shaft 220 further comprises one or more grooves. In the embodiment shown, central shaft 220 comprises grooves 232A (not shown) and 232B. In some embodiments, grooves 232A and 232B are arranged diametrically opposite each other. End 224 is connected to collar 240. Specifically, end 224 is non-rotatably connected to portion 240A, as will be discussed in greater detail below. Teeth 226 engage collar 250, specifically engaging member 257, to allow collar 250 to move in axial direction AD1 (but not in axial direction AD2) to expand and contract expansion cage 260, as will be discussed in greater detail below. Grooves 232A and 232B also engage collar 250, specifically protrusions 256A and 256B, to non-rotatably but slidably connect collar 250 to central shaft 220. As such, when collar 250 is rotated central shaft 220 rotates at the same rotational speed. In some embodiments, central shaft 220 comprises one or more holes. In the embodiment shown, central shaft 220 comprises hole 334. Once expandable facet joint fixation device 210 is expanded as desired, bone putty or bone fusion material can be pumped into central shaft 220 through end 222, and then into the cavity created by expandable facet joint fixation device 210, as will be discussed in greater detail below. Hole 234 allows the bone putty pumped into central shaft 220 through end 222 to flow into the cavity created by expandable facet joint fixation device 210.

Collar 240 comprises portion 240A, portion 240B, and bearing 245. Portion 240A comprises surface 241A, surface 241B, hole 242, radially outward facing surface 244, and tip 246. Hole 242 extends from surface 241B in axial direction AD1 and is arranged to engage bearing 245. Portion 240B comprises surface 247A, surface 247B, hole 249, and radially outward facing surface 248. Hole 249 extends from surface 247A in axial direction AD2 and is arranged to engage bearing 245. Bearing 245 extends, at least partially, into hole 242 and hole 249. Bearing 245 may be any bearing suitable to allow rotation between portion 240A and 240B, for example, a ball bearing, roller bearing, ball thrust bearing, roller thrust bearing, or tapered roller bearing. When collar 240 is fully assembled, portion 240B is axially fixed and rotatably connected to portion 240A. End 224 of central shaft 220 is non-rotatably connected to surface 247B of portion 240. Tip 246 extends from surface 241A in axial direction AD1. Tip 246 is arranged to engage a bone, joint, or facet joint, to provide an anchor for skeletal traction. Tip 246 may, for example, engage cartilage in the facet joint, as will be discussed in greater detail below. In the embodiment shown, collar 240, specifically, radially outward facing surfaces 244 and 248, is cylindrical with a circular cross-section. However, it should be appreciated that radially outward facing surfaces 244 and 248 may comprise any geometry (e.g., square, rectangular, ovular, trapezoidal, etc.) suitable for securing hinges 268A-D, as will be discussed in greater detail below.

Collar 250 is generally an annular ring comprising radially inward facing surface 252 and radially outward facing surface 254. Radially inward facing surface 252 comprises one or more protrusions arranged to engage central shaft 220. In the embodiment shown, radially inward facing surface 252 comprises protrusions 256A and 256B which engage grooves 232A and 232B, respectively, of central shaft 220. The engagement of protrusions 256A and 256B with grooves 232A and 232B allow for the non-rotatable connection of collar 250 to central shaft 220. As collar 250 is being rotated, thus rotating expansion cage 260 for cutting, collar 250 can be slid along central shaft 220 and displaced toward collar 240 (i.e., the distance between collars 240 and 250 is reduced) to further expand expandable members 262A-D, as will be discussed in greater detail below. In some embodiments, radially inward facing surface 252 may further comprise engaging member 257 extending radially inward therefrom. Engaging member 257 is arranged to engage teeth 226 to allow collar 250 to move in axial direction AD1 but not in axial direction AD2. This allows for the gradual expansion of expansion cage 260 and maintains the current expanded state (i.e., prevents collar 250 from displacing in axial direction AD2 and thus contraction of expansion cage 260). In some embodiments, collar 250 further comprises release 259. Release 259 is arranged to, when activated, disengage engaging member 257 from teeth 226 to allow collar 250 to be displaced in axial direction AD2. In some embodiments, engaging member 257 is an elastically deformable material such that, a user can, with enough force, overcome the interference between engaging member 257 and teeth 226 and displace collar 250 in axial direction AD2, and continue to use expandable facet joint fixation device 210. In some embodiments, engaging member 257 is a plastically deformable material such that, a user can, with enough force, overcome the interference between engaging member 257 and teeth 226 and displace collar 250 in axial direction AD2. However, since engaging member 257 is plastically deformable, expandable facet joint fixation device 210 must then be discarded. As previously mentioned, when collar 250 is displaced in axial direction AD1 relative to collar 240, expansion cage 260 expands in radial direction RD1. When collar 250 displaces in axial direction AD2 relative to collar 240, expansion cage 260 contracts in radial direction RD2. In some embodiments, radially outward facing surface 254 comprises engaging component 258 to be non-rotatable connected to outer sleeve 280, as will be discussed in greater detail below. For example, engaging component 258 may be a hex head or have a protrusion that outer sleeve 280 can slide over, similar to a socket and bolt. It should be appreciated, however, that any engaging component suitable for non-rotatable connection to an outer sleeve may be used. In the embodiment shown, collar 250, specifically, radially outward facing surface 254, is cylindrical with a circular cross-section. However, it should be appreciated that radially outward facing surface 254 may comprise any geometry (e.g., square, rectangular, ovular, trapezoidal, etc.) suitable for securing hinges 264A-D, as will be discussed in greater detail below.

Expansion cage 260 comprises a plurality of arms and hinges. In some embodiments, expansion cage 260 may comprise one or more expandable members, with each expandable member including one or more hinges and one or more arms. In the embodiment shown, expansion cage 260 comprises expandable members 262A-D, as is discussed in greater detail below.

Expandable member 262A comprises hinge 264A, hinge 266A, hinge 268A, arm 270A, and arm 272A. Arm 270A is hingedly connected to collar 250 via hinge 264A. Arm 272A is hingedly connected to arm 270A via hinge 266A. Arm 272A is hingedly connected to collar 240 via hinge 268A. As collar 250 is displaced in axial direction AD1 relative to collar 240 (i.e., the distance between collars 240 and 250 decreases), arm 270A, arm 272A, and hinge 266A expand radially outward in radial direction RD1. As collar 250 is displaced in axial direction AD2 relative to collar 240 (i.e., the distance between collars 240 and 250 increases), arm 270A, arm 272A, and hinge 266A contract radially inward in radial direction RD2. In some embodiments, arms 270A and 272A comprise cutting surfaces 274A and 276A, respectively. As expandable facet joint fixation device 210, specifically expansion cage 260, is rotated about axis of rotation 212 in circumferential direction CD1 and/or CD2, cutting surfaces 274A and 276A cut into adjacent bone to create a cavity, as was previously discussed with respect to FIGS. 4-10 above.

Expandable member 262B comprises hinge 264B, hinge 266B, hinge 268B, arm 270B, and arm 272B. Arm 270B is hingedly connected to collar 250 via hinge 264B. Arm 272B is hingedly connected to arm 270B via hinge 266B. Arm 272B is hingedly connected to collar 240 via hinge 268B. As collar 250 is displaced in axial direction AD1 relative to collar 240 (i.e., the distance between collars 240 and 250 decreases), arm 270B, arm 272B, and hinge 266B expand radially outward in radial direction RD1. As collar 250 is displaced in axial direction AD2 relative to collar 240 (i.e., the distance between collars 240 and 250 increases), arm 270B, arm 272B, and hinge 266B contract radially inward in radial direction RD2. In some embodiments, arms 270B and 272B comprise cutting surfaces 274B and 276B, respectively. As expandable facet joint fixation device 210, specifically expansion cage 260, is rotated about axis of rotation 212 in circumferential direction CD1 and/or CD2, cutting surfaces 274B and 276B cut into adjacent bone to create a cavity, as was previously discussed with respect to FIGS. 4-10 above.

Expandable member 262C comprises hinge 264C, hinge 266C, hinge 268C, arm 270C, and arm 272C. Arm 270C is hingedly connected to collar 250 via hinge 264C. Arm 272C is hingedly connected to arm 270C via hinge 266C. Arm 272C is hingedly connected to collar 240 via hinge 268C. As collar 250 is displaced in axial direction AD1 relative to collar 240 (i.e., the distance between collars 240 and 250 decreases), arm 270C, arm 272C, and hinge 266C expand radially outward in radial direction RD1. As collar 250 is displaced in axial direction AD2 relative to collar 240 (i.e., the distance between collars 240 and 250 increases), arm 270C, arm 272C, and hinge 266C contract radially inward in radial direction RD2. In some embodiments, arms 270C and 272C comprise cutting surfaces 274C and 276C, respectively. As expandable facet joint fixation device 210, specifically expansion cage 260, is rotated about axis of rotation 212 in circumferential direction CD1 and/or CD2, cutting surfaces 274C and 276C cut into adjacent bone to create a cavity, as was previously discussed with respect to FIGS. 4-10 above.

Expandable member 262D comprises hinge 264D, hinge 266D, hinge 268D, arm 270D, and arm 272D. Arm 270D is hingedly connected to collar 250 via hinge 264D. Arm 272D is hingedly connected to arm 270D via hinge 266D. Arm 272D is hingedly connected to collar 240 via hinge 268D. As collar 250 is displaced in axial direction AD1 relative to collar 240 (i.e., the distance between collars 240 and 250 decreases), arm 270D, arm 272D, and hinge 266D expand radially outward in radial direction RD1. As collar 250 is displaced in axial direction AD2 relative to collar 240 (i.e., the distance between collars 240 and 250 increases), arm 270D, arm 272D, and hinge 266D contract radially inward in radial direction RD2. In some embodiments, arms 270D and 272D comprise cutting surfaces 274D and 276D, respectively. As expandable facet joint fixation device 210, specifically expansion cage 260, is rotated about axis of rotation 212 in circumferential direction CD1 and/or CD2, cutting surfaces 274D and 276D cut into adjacent bone to create a cavity, as was previously discussed with respect to FIGS. 4-10 above.

Outer sleeve 280 comprises end 282, end 284, and socket 286. Outer sleeve 280 is arranged to removably and non-rotatably connect to collar 250. Specifically, socket 286 engages engaging component 258. As previously mentioned, collar 250 is rotated to in turn rotate expansion cage 260. As collar 250 is rotated, central shaft 220 rotates at the same rate. As such, outer sleeve 280 allows the user to rotate collar 250 and central shaft 220 for cutting action. In cutting mode, a drill may be used to rotate both central shaft 220 and collar 250 at the same rotational speed, which allows expandable facet joint fixation device 210 to rotate about axis of rotation 212 without expansion cage 260 expanding or contracting (i.e., the distance between collars 240 and 250 remains constant). This can be envisioned by using a drill and a drill attachment which non-rotatably connects to outer sleeve 280. In expansion mode, collar 250 is displaced in axial direction AD1 (i.e., the distance between collars 240 and 250 decreases) to expand expansion cage 260 in radial direction RD1. Additionally, as collar 250, central shaft 220, and expansion cage 260 are being rotated (i.e., for cutting mode), the user can displace collar 250 in axial direction AD1 (i.e., the distance between collars 240 and 250 decreases) to expand expansion cage 260 in radial direction RD1 (i.e., expansion mode). The design of expandable facet joint fixation device 210 allows the user to expand the implant radially while cutting away the adjacent bone of the articular processes. As collar 250 is displaced in axial direction AD1, engaging member 257 engages teeth 226 thereby locking collar 250 at a location on central shaft 220. As previously discussed, the engagement of engaging member 257 with teeth 226 allows movement of collar 250 in axial direction AD1 but not axial direction AD2. In some embodiments, release 259 is arranged to, when activated, disengage engaging member 257 from teeth 226 to allow movement of collar 250 in axial direction AD2. Once a cavity of a desired size is formed in the facet joint, collar 250 is displaced in axial direction AD1 such that expandable members 262A-D are pressed tightly against the adjacent articular processes, and outer sleeve 280 is removed from collar 250. Bone putty or bony or biologic material is then injected into central shaft 220 through end 222. The bone putty flows out of hole 234 and to adjacent articular processes and hence can foster interbody fusion. In an example embodiment, bony growth and permanent fixation may be achieved with hardenable materials such as bone putty or methyl methylacrylate (MMA) as is known to those having ordinary skill in the art.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Expandable facet joint fixation device
12 Axis of rotation
20 Central shaft
20A Portion
20B Portion
22 End
24 End
25 Radially outward facing surface
26 Threading
28 Break plane
30 Wrench
32 Socket
34A Hole
34B Hole
34C Hole
36 Tip
40 Collar
41A Surface
41B Surface
42 Hole
44 Radially outward facing surface
46 Tip
50 Collar
52 Radially inward facing surface
54 Radially outward facing surface
56 Threading
58 Engaging component
60 Expansion cage
62A Expandable member
62B Expandable member
62C Expandable member
62D Expandable member
64A Hinge
64B Hinge
64C Hinge
64D Hinge
66A Hinge
66B Hinge
66C Hinge
66D Hinge
68A Hinge
68B Hinge
68C Hinge
68D Hinge
70A Arm
70B Arm
70C Arm
70D Arm
72A Arm
72B Arm
72C Arm
72D Arm
74A Cutting surface
74B Cutting surface
74C Cutting surface
74D Cutting surface
76A Cutting surface
76B Cutting surface 76C Cutting surface
76D Cutting surface
80 Outer sleeve
82 End
84 End
86 Socket
100 Vertebra
102 Spinous process
104 Inferior articular process
106 Vertebral body
108 Superior articular process
110 Vertebral foramen 112 Facet joint
120 K-wire
122 Drill
124 Hole
210 Expandable facet joint fixation device
212 Axis of rotation
220 Central shaft
222 End
223 Radially inward facing surface
224 End
225 Radially outward facing surface
226 Teeth
232A Groove
232B Groove
234 Hole(s)
240 Collar
240A Portion
240B Portion
241A Surface
241B Surface
242 Hole
244 Radially outward facing surface
245 Bearing
246 Tip
247A Surface
247B Surface
248 Radially outward facing surface
249 Hole
250 Collar
252 Radially inward facing surface
254 Radially outward facing surface
256A Protrusion
256B Protrusion
257 Engaging member
258 Engaging component
259 Release
260 Expansion cage
262A Expandable member
262B Expandable member
262C Expandable member
262D Expandable member
264A Hinge
264B Hinge
264C Hinge
264D Hinge
266A Hinge
266B Hinge
266C Hinge
266D Hinge
268A Hinge
268B Hinge
268C Hinge
268D Hinge
270A Arm
270B Arm
270C Arm
270D Arm
272A Arm
272B Arm
272C Arm
272D Arm
274A Cutting surface
274B Cutting surface
274C Cutting surface
274D Cutting surface
276A Cutting surface
276B Cutting surface
276C Cutting surface
276D Cutting surface
280 Outer sleeve
282 End
284 End
286 Socket
AD1 Axial direction
AD2 Axial direction
RD1 Radial direction
RD2 Radial direction
CD1 Circumferential direction
CD2 Circumferential direction

What is claimed is:

1. An expandable facet joint fixation device, comprising:
a first collar;
a central shaft including a first end and a second end, the first end rotatably connected to the first collar;
a second collar including a radially inward facing surface, the second collar concentrically arranged around the central shaft; and,
one or more expandable members, each of the one or more expandable members including:
a first arm hingedly connected to the first collar; and,
a second arm hingedly connected to the second collar, the second arm hingedly connected to the first arm, wherein at least one of the one or more expandable members comprises at least one cutting surface wherein the at least one cutting surface is arranged to be rotated to cut through cortical bone;
wherein when the second collar is displaced in a first axial direction relative to the first collar, the one or more expandable members displace radially outward in a first radial direction.

2. The expandable facet joint fixation device as recited in claim 1, wherein the second collar is threadably engaged with the central shaft.

3. The expandable facet joint fixation device as recited in claim 1, wherein each of the one or more expandable members comprises:
a first cutting surface arranged on the first arm; and,
a second cutting surface arranged on the second arm.

4. The expandable facet joint fixation device as recited in claim 1, further comprising an outer sleeve arranged to be removably and non-rotatably connected to the second collar.

5. The expandable facet joint fixation device as recited in claim 4, wherein the second collar further comprises an engaging component and the outer sleeve comprises a socket, the socket being arranged to engage the engaging component to removably and non-rotatably connect the outer sleeve to the second collar.

6. The expandable facet joint fixation device as recited in claim 1, wherein the central shaft further comprises a first portion and a second portion, the first portion arranged to removably and non-rotatably connect to the second portion.

7. The expandable facet joint fixation device as recited in claim 6, wherein the second portion is a hollow tube.

8. The expandable facet joint fixation device as recited in claim 7, wherein the second portion further comprises one or more holes.

9. The expandable facet joint fixation device as recited in claim 8, wherein bone fusion material is injected into the second portion and flows out of the one or more holes to engage adjacent articular processes and fuse the facet joint.

10. The expandable facet joint fixation device as recited in claim 6, wherein the first portion comprises a wrench and the second portion comprises a socket, the wrench arranged to engage the socket to non-rotatably connect the first portion with the second portion.

11. An expandable joint fixation device, comprising:
an expansion cage, including:
a first collar;
a second collar having a radially inward facing surface with interior threading; and,
one or more expandable members, at least one of the one or more expandable members includes at least one cutting surface; and,
a central shaft extending through the second collar, the central shaft including:
a first end rotatably connected to the first collar; and,
a radially outward facing surface having exterior threading, the exterior threading being threadably engaged with the interior threading;
wherein:
when the second collar is displaced in a first axial direction relative to the first collar, the one or more expandable members displace radially outward in a first radial direction; and,
the one or more expandable members are operatively arranged to be rotated to cut through cortical bone.

12. The expandable joint fixation device as recited in claim 11, wherein each of the one or more expandable members comprises:
a first arm hingedly connected to the first collar, the first arm including a first cutting surface; and,
a second arm hingedly connected to the second collar and the first arm, the second arm including a second cutting surface.

13. The expandable joint fixation device as recited in claim 12, wherein in an unexpanded state, the first arm and the second arm of each of the one or more expandable members abuts against the radially outward facing surface.

14. The expandable joint fixation device as recited in claim 11, further comprising an outer sleeve arranged to be removably and non-rotatably connected to the second collar.

15. The expandable joint fixation device as recited in claim 11, wherein the central shaft further comprises a first portion and a second portion, the first portion arranged to removably and non-rotatably connect to the second portion.

16. The expandable joint fixation device as recited in claim 15, wherein the second portion is a hollow tube.

17. The expandable joint fixation device as recited in claim 16, wherein the second portion further comprises one or more holes.

18. The expandable joint fixation device as recited in claim 16, wherein bone fusion material is injected into the second portion and flows out of the one or more holes to engage adjacent articular processes and fuse the facet joint.

19. An expandable joint fixation device, comprising:
an expansion cage, including:
a first collar;
a second collar having a radially inward facing surface with interior threading; and,
one or more expandable members, each of the one or more expandable members hingedly connected to the first and second collars, wherein at least one of the one or more expandable members includes at least one cutting surface operatively arranged to cut through cortical bone; and,
a central shaft extending through the second collar, the central shaft being hollow and including:
a first end rotatably connected to the first collar;
a radially outward facing surface having exterior threading threadably engaged with the interior threading; and,
one or more holes;
wherein:
when the central shaft is rotated in a first circumferential direction, relative to the second collar, the second collar is displaced in a first axial direction relative to the first collar and the one or more expandable members displace radially outward in a first radial direction; and,
when the central shaft is rotated in a second circumferential direction, opposite the first circumferential direction, relative to the second collar, the second collar is displaced in a second axial direction, opposite the first axial direction, relative to the first collar and the one or more expandable members displace radially inward in a second radial direction, opposite the first radial direction.

* * * * *